(12) United States Patent
Robertson et al.

(10) Patent No.: US 9,918,966 B2
(45) Date of Patent: Mar. 20, 2018

(54) ANTI-CANCER COMPOSITIONS AND METHODS

(71) Applicant: The Penn State Research Foundation, University Park, PA (US)

(72) Inventors: Gavin P. Robertson, Hummelstown, PA (US); Chandagalu D. Raghavendra Gowda, Hershey, PA (US); Dhimant H. Desai, Mechanicsburg, PA (US); Shantu G. Amin, Union City, NJ (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/244,671

(22) Filed: Aug. 23, 2016

(65) Prior Publication Data

US 2016/0354344 A1 Dec. 8, 2016

Related U.S. Application Data

(62) Division of application No. 14/734,564, filed on Jun. 9, 2015, now Pat. No. 9,439,887, which is a division
(Continued)

(51) Int. Cl.
| | |
|---|---|
| *A61K 31/095* | (2006.01) |
| *A61K 31/415* | (2006.01) |
| *A61K 45/06* | (2006.01) |
| *A61K 9/127* | (2006.01) |
| *A61K 9/00* | (2006.01) |
| *A61K 38/06* | (2006.01) |
| *C07D 231/12* | (2006.01) |

(Continued)

(52) U.S. Cl.
CPC .......... *A61K 31/415* (2013.01); *A61K 9/0014* (2013.01); *A61K 9/127* (2013.01); *A61K 9/1271* (2013.01); *A61K 38/063* (2013.01); *A61K 45/06* (2013.01); *C07D 231/12* (2013.01); *A61K 31/095* (2013.01); *C07D 231/10* (2013.01); *C07D 231/42* (2013.01)

(58) Field of Classification Search
CPC ................................................... A61K 31/095
See application file for complete search history.

(56) References Cited

U.S. PATENT DOCUMENTS

| | | |
|---|---|---|
| 5,466,823 A | 11/1995 | Talley et al. |
| 5,563,165 A | 10/1996 | Talley et al. |

(Continued)

OTHER PUBLICATIONS

Desai et al. (International Journal of Cancer, vol. 127, 2010, pp. 230-238).*

(Continued)

*Primary Examiner* — Benjamin Packard
(74) *Attorney, Agent, or Firm* — Dinsmore & Shohl LLP

(57) ABSTRACT

Compositions and pharmaceutical compositions including one or more selenium-containing COX-2 inhibitors are provided according to aspects of the present invention. Methods of treating a subject having or suspected of having cancer are provided according to aspects of the present invention which include administering a therapeutically effective amount of a pharmaceutical composition including a selenium-containing COX-2 inhibitor.

10 Claims, 25 Drawing Sheets

Related U.S. Application Data of application No. 14/169,639, filed on Jan. 31, 2014, now Pat. No. 9,107,947.

(60) Provisional application No. 61/759,034, filed on Jan. 31, 2013.

(51) Int. Cl.
  *C07D 231/42* (2006.01)
  *C07D 231/10* (2006.01)

(56) References Cited

U.S. PATENT DOCUMENTS

| | | | |
|---|---|---|---|
| 5,760,068 A | 6/1998 | Talley et al. | |
| 2001/0038851 A1* | 11/2001 | Allen | A61K 9/127 424/450 |

OTHER PUBLICATIONS

Desai et al. (Chemico-Biological Interactions, vol. 188, 2010, pp. 446-456).*

Balendiran, G. et al., "The Role of Glutathione in Cancer," *Cell Biochemistry and Function*, 22: 343-352, 2004.

Desai, D. et al., Synthesis and antitumor properties of selenoxcoxib-1 against rat prostate adenocarcinoma cells, *International Journal of Cancer*, 127: 230-38, 2010.

Desai, D. et al., Synthesis and evaluation of the anti-inflammatory properties of selenium-derivatives of celecoxib, *Chemico-Biological Interactions*, 188: 446-56, 2010.

Gowda, R. et al., Simultaneous Targeting of COX-2 and AKT Using Selenocoxib-1-GSH to Inhibit Melanoma, *American Association for Cancer Research, Molecular Cancer Therapeutics*, 12(1): 3-15, Oct. 30, 2012.

Hawk, E. et al., COX-2 in Cancer—A Player That's Defining the Rules, *Journal of the National Cancer Institute, Editorials*, 94(8): 545-46, Apr. 17, 2002.

Penning, T. et al., Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib, *J. Med. Chem.*, 40: 1347-65, 1997.

* cited by examiner

SEQUENCE LISTING

<160> NUMBER OF SEQ ID NOS: 2

<210> SEQ ID NO 1
<211> LENGTH: 25
<212> TYPE: RNA
<213> ORGANISM: Artificial Sequence
<220> FEATURE:
<223> OTHER INFORMATION: COX-2 siRNA

<400> SEQUENCE: 1
uccagacaag caggcuaaua cugau          25

<210> SEQ ID NO 2
<211> LENGTH: 25

```
<212> TYPE: RNA
<213> ORGANISM: Artificial Sequence
<220> FEATURE:
<223> OTHER INFORMATION: COX-2 siRNA

<400> SEQUENCE: 2
gaguuauguc uugacaucca gauca                                              25
```

ANTI-CANCER COMPOSITIONS AND METHODS

REFERENCE TO RELATED APPLICATIONS

This application is a divisional of U.S. patent application Ser. No. 14/734,564, filed Jun. 9, 2015, which is a divisional of U.S. patent application Ser. No. 14/169,639, filed Jan. 31, 2014, now U.S. Pat. No. 9,107,947, which claims priority from U.S. Provisional Patent Application Ser. No. 61/759,034, filed Jan. 31, 2013, the entire content of all of which is incorporated herein by reference.

GOVERNMENT SPONSORSHIP

The invention was made with government support under Grant Nos. CA127892 and CA136667 awarded by The National Institutes of Health. The Government has certain rights in the invention.

FIELD OF THE INVENTION

The present invention relates generally to anti-cancer compositions and methods. In specific aspects, the present invention relates to compositions including one or more selenium-containing cyclooxygenase-2 (COX-2) inhibitor compounds, methods for treatment and/or prevention of pathological conditions in a subject using one or more selenium-containing COX-2 inhibitor compounds and methods for synthesis of particular selenium-containing COX-2 inhibitor compounds.

BACKGROUND OF THE INVENTION

In spite of recent medical progress, cancer continues to be one of the most common and deadly diseases. Elucidation of biochemical pathways involved in development and progression of various cancers is important to identify potential anti-cancer treatments as well as to develop agents effective to regulate such pathways in other aspects of health and disease.

Compositions and methods are required to inhibit cancer cell survival and proliferation. In particular, compositions and methods are required to inhibit COX-2 activity in cancer cells, reduce survival and/or reduce proliferation of cancer cells.

SUMMARY OF THE INVENTION

Compositions including one or more selenium-containing COX-2 inhibitors are provided according to aspects of the present invention.

Compositions including a selenium-containing COX-2 inhibitor are provided according to aspects of the present invention, wherein the selenium-containing COX-2 inhibitor is selenocoxib-1-glutathione (selenocoxib-1-GSH).

Compositions including a selenium-containing COX-2 inhibitor are provided according to aspects of the present invention, wherein the selenium-containing COX-2 inhibitor is selenocoxib-1-cysteine.

Compositions including a selenium-containing COX-2 inhibitor are provided according to aspects of the present invention, wherein the selenium-containing COX-2 inhibitor is selenocoxib-1-N-aceyl cysteine (selenocoxib-1-NAC).

Pharmaceutical compositions including one or more selenium-containing COX-2 inhibitors and a pharmaceutically acceptable carrier are provided according to aspects of the present invention.

Pharmaceutical compositions including: a pharmaceutically acceptable carrier; and one or more of: selenocoxib-1-GSH, selenocoxib-1-cysteine and selenocoxib-1-NAC, are provided according to aspects of the present invention.

Pharmaceutical compositions including one or more selenium-containing COX-2 inhibitors and a pharmaceutically acceptable carrier are provided according to aspects of the present invention, wherein the pharmaceutical composition is formulated for topical application.

Pharmaceutical compositions including: a pharmaceutically acceptable carrier; and one or more of: selenocoxib-1-GSH, selenocoxib-1-cysteine and selenocoxib-1-NAC, are provided according to aspects of the present invention, wherein the pharmaceutical composition is formulated for topical application.

Pharmaceutical compositions including one or more selenium-containing COX-2 inhibitors and a pharmaceutically acceptable carrier are provided according to aspects of the present invention, wherein the pharmaceutically acceptable carrier includes a particulate carrier.

Pharmaceutical compositions including: a pharmaceutically acceptable carrier; and one or more of: selenocoxib-1-GSH, selenocoxib-1-cysteine and selenocoxib-1-NAC, are provided according to aspects of the present invention, wherein the pharmaceutically acceptable carrier includes a particulate carrier.

Pharmaceutical compositions including one or more selenium-containing COX-2 inhibitors and a pharmaceutically acceptable carrier are provided according to aspects of the present invention, wherein the pharmaceutically acceptable carrier includes a nanoparticulate carrier.

Pharmaceutical compositions including: a pharmaceutically acceptable carrier; and one or more of: selenocoxib-1-GSH, selenocoxib-1-cysteine and selenocoxib-1-NAC, are provided according to aspects of the present invention, wherein the pharmaceutically acceptable carrier includes a nanoparticulate carrier.

Pharmaceutical compositions including a plurality of nanoliposomes are provided according to aspects of the present invention, wherein the nanoliposomes include selenocoxib-1-GSH, selenocoxib-1-cysteine or selenocoxib-1-NAC; or two or more thereof, and wherein the nanoliposomes have an average particle size in the range of 1-100 nm.

Pharmaceutical compositions including one or more selenium-containing COX-2 inhibitors, one or more additional therapeutic agents, and a pharmaceutically acceptable carrier are provided according to aspects of the present invention.

Pharmaceutical compositions including: a pharmaceutically acceptable carrier; one or more of: selenocoxib-1-GSH, selenocoxib-1-cysteine and selenocoxib-1-NAC; and one or more additional therapeutic agents, are provided according to aspects of the present invention.

Methods of treating a subject are provided according to aspects of the present invention which include administering a therapeutically effective amount of a pharmaceutical composition including a selenium-containing COX-2 inhibitor. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

According to aspects of the present invention, methods of treating a subject include administering a therapeutically effective amount of a pharmaceutical composition including selenocoxib-1-GSH, selenocoxib-1-cysteine or selenocoxib-1-NAC; or two or more thereof. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

Methods of treating a subject having or suspected of having cancer are provided according to aspects of the present invention which include administering a therapeutically effective amount of a pharmaceutical composition including a selenium-containing COX-2 inhibitor. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

According to aspects of the present invention, methods of treating a subject having or suspected of having cancer include administering a therapeutically effective amount of a pharmaceutical composition including selenocoxib-1-GSH, selenocoxib-1-cysteine or selenocoxib-1-NAC; or two or more thereof. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

Methods of treating a subject having or suspected of having breast cancer, lung cancer, prostate cancer, colon cancer, liver cancer or melanoma are provided according to aspects of the present invention which include administering a therapeutically effective amount of a pharmaceutical composition including a selenium-containing COX-2 inhibitor. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

According to aspects of the present invention, methods of treating a subject having or suspected of having breast cancer, lung cancer, prostate cancer, colon cancer, liver cancer or melanoma include administering a therapeutically effective amount of a pharmaceutical composition including selenocoxib-1-GSH, selenocoxib-1-cysteine or selenocoxib-1-NAC; or two or more thereof. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

Methods of treating a subject wherein the subject has or is suspected of having cancer characterized by increased COX-2 protein or nucleic acid, increased COX-2 activity and/or increased Akt activity compared to a control are provided according to aspects of the present invention which include administering a therapeutically effective amount of a pharmaceutical composition including a selenium-containing COX-2 inhibitor. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

According to aspects of the present invention, methods of treating a subject wherein the subject has or is suspected of having cancer characterized by increased COX-2 protein or nucleic acid, increased COX-2 activity and/or increased Akt activity compared to a control include administering a therapeutically effective amount of a pharmaceutical composition including selenocoxib-1-GSH, selenocoxib-1-cysteine or selenocoxib-1-NAC; or two or more thereof. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

Methods of treating a subject wherein the subject has or is suspected of having breast cancer, lung cancer, prostate cancer, colon cancer, liver cancer or melanoma characterized by increased COX-2 protein or nucleic acid, increased COX-2 activity and/or increased Akt activity compared to a control are provided according to aspects of the present invention which include administering a therapeutically effective amount of a pharmaceutical composition including a selenium-containing COX-2 inhibitor. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

According to aspects of the present invention, methods of treating a subject wherein the subject has or is suspected of having breast cancer, lung cancer, prostate cancer, colon cancer, liver cancer or melanoma characterized by increased COX-2 protein or nucleic acid, increased COX-2 activity and/or increased Akt activity compared to a control include administering a therapeutically effective amount of a pharmaceutical composition including selenocoxib-1-GSH, selenocoxib-1-cysteine or selenocoxib-1-NAC; or two or more thereof. The subject is a human according to aspects of the present invention. Optionally, the pharmaceutical composition is formulated as a topical composition. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition.

Administering a therapeutically effective amount of a pharmaceutical composition including a selenium-containing COX-2 inhibitor to a subject having or suspected of having cancer according to aspects of methods of treatment of the present invention detectably increases apoptosis and/or decreases proliferation of cells of the cancer and has negligible effect on non-cancer cells. Further, administering a therapeutically effective amount of a pharmaceutical composition including a selenium-containing COX-2 inhibitor to the subject having or suspected of having cancer according to aspects of methods of treatment of the present invention detectably decreases free radicals and/or reactive oxygen species of cells of the cancer and has negligible effect on non-cancer cells.

Administering a therapeutically effective amount of a pharmaceutical composition including selenocoxib-1-GSH, selenocoxib-1-cysteine or selenocoxib-1-NAC; or two or more thereof, to a subject having or suspected of having cancer according to aspects of methods of treatment of the present invention detectably increases apoptosis and/or decreases proliferation of cells of the cancer and has negligible effect on non-cancer cells. Further, administering a therapeutically effective amount of a pharmaceutical composition including selenocoxib-1-GSH, selenocoxib-1-cysteine or selenocoxib-1-NAC; or two or more thereof, to the subject having or suspected of having cancer according to aspects of methods of treatment of the present invention detectably decreases free radicals and/or reactive oxygen species of cells of the cancer and has negligible effect on non-cancer cells.

Administering a therapeutically effective amount of a pharmaceutical composition including a selenium-containing COX-2 inhibitor to a subject having or suspected of having breast cancer, lung cancer, prostate cancer, colon cancer, liver cancer or melanoma according to aspects of methods of treatment of the present invention detectably increases apoptosis and/or decreases proliferation of cells of the cancer and has negligible effect on non-cancer cells. Further, administering a therapeutically effective amount of a pharmaceutical composition including a selenium-containing COX-2 inhibitor to the subject having or suspected of having breast cancer, lung cancer, prostate cancer, colon cancer, liver cancer or melanoma according to aspects of methods of treatment of the present invention detectably decreases free radicals and/or reactive oxygen species of cells of the cancer and has negligible effect on non-cancer cells.

Administering a therapeutically effective amount of a pharmaceutical composition including selenocoxib-1-GSH, selenocoxib-1-cysteine or selenocoxib-1-NAC; or two or more thereof, to a subject having or suspected of having breast cancer, lung cancer, prostate cancer, colon cancer, liver cancer or melanoma according to aspects of methods of treatment of the present invention detectably increases apoptosis and/or decreases proliferation of cells of the cancer and has negligible effect on non-cancer cells. Further, administering a therapeutically effective amount of a pharmaceutical composition including selenocoxib-1-GSH, selenocoxib-1-cysteine or selenocoxib-1-NAC; or two or more thereof to the subject having or suspected of having breast cancer, lung cancer, prostate cancer, colon cancer, liver cancer or melanoma according to aspects of methods of treatment of the present invention detectably decreases free radicals and/or reactive oxygen species of cells of the cancer and has negligible effect on non-cancer cells.

Selenium-containing COX-2 inhibitor compounds of the present invention target COX-2 and Akt signaling in cancer cells such that expression and/or activity of these proteins or any downstream member of these signaling cascades is used to identify patients in need of treatment with selenium-containing COX-2 inhibitor compounds of the present invention, and/or to measure the therapeutic efficacy of such treatment. Thus, according to aspects of the present invention, methods of treating a subject having or suspected of having cancer such as, but not limited to, breast cancer, lung cancer, prostate cancer, colon cancer, liver cancer and melanoma, includes assaying assaying COX-2 protein, COX-2 nucleic acid, COX-2 activity and/or Akt activity in cells of the cancer or putative cancer, prior to and/or after administration of a selenium-containing COX-2 inhibitor of the present invention to the subject.

According to aspects of the present invention, methods of treating a subject having or suspected of having cancer such as, but not limited to, breast cancer, lung cancer, prostate cancer, colon cancer, liver cancer and melanoma, includes assaying assaying COX-2 protein, COX-2 nucleic acid, COX-2 activity and/or Akt activity in cells of the cancer or putative cancer, prior to and/or after administration of selenocoxib-1-GSH, selenocoxib-1-cysteine, selenocoxib-1-NAC or two or more of selenocoxib-1-GSH, selenocoxib-1-cysteine and selenocoxib-1-NAC, to the subject.

Methods of treating a subject having or suspected of having cancer according to aspects of the present invention include assaying COX-2 protein, COX-2 nucleic acid, COX-2 activity and/or Akt activity in cells of the cancer prior to and/or after administration of a pharmaceutical composition including a selenium-containing COX-2 inhibitor to the subject to determine the level of expression of COX-2 protein in the cells of the cancer compared to a control, the level of expression of COX-2 nucleic acid in the cells of the cancer compared to a control, the level of activity of COX-2 in the cells of the cancer compared to a control and/or the level of activity of Akt in the cells of the cancer compared to a control.

Methods of treating a subject having or suspected of having cancer according to aspects of the present invention include assaying COX-2 protein, COX-2 nucleic acid, COX-2 activity and/or Akt activity in cells of the cancer prior to and/or after administration of a pharmaceutical composition including selenocoxib-1-GSH, selenocoxib-1-cysteine or selenocoxib-1-NAC; or two or more thereof, to the subject to determine the level of expression of COX-2 protein in the cells of the cancer compared to a control, the level of expression of COX-2 nucleic acid in the cells of the cancer compared to a control, the level of activity of COX-2 in the cells of the cancer compared to a control and/or the level of activity of Akt in the cells of the cancer compared to a control.

Methods of treating a subject having or suspected of having breast cancer, lung cancer, prostate cancer, colon cancer, liver cancer or melanoma according to aspects of the present invention include assaying COX-2 protein, COX-2 nucleic acid, COX-2 activity and/or Akt activity in cells of the breast cancer, lung cancer, prostate cancer, colon cancer, liver cancer or melanoma prior to and/or after administration of a pharmaceutical composition including a selenium-containing COX-2 inhibitor to the subject to determine the level of expression of COX-2 protein in the cells of the breast cancer, lung cancer, prostate cancer, colon cancer, liver cancer or melanoma compared to a control, the level of expression of COX-2 nucleic acid in the cells of the breast cancer, lung cancer, prostate cancer, colon cancer, liver cancer or melanoma compared to a control, the level of activity of COX-2 in the cells of the breast cancer, lung cancer, prostate cancer, colon cancer, liver cancer or melanoma compared to a control and/or the level of activity of Akt in the cells of the breast cancer, lung cancer, prostate cancer, colon cancer, liver cancer or melanoma compared to a control.

Methods of treating a subject having or suspected of having breast cancer, lung cancer, prostate cancer, colon cancer, liver cancer or melanoma according to aspects of the present invention include assaying COX-2 protein, COX-2 nucleic acid, COX-2 activity and/or Akt activity in cells of the breast cancer, lung cancer, prostate cancer, colon cancer, liver cancer or melanoma prior to and/or after administration of a pharmaceutical composition including selenocoxib-1-GSH, selenocoxib-1-cysteine or selenocoxib-1-NAC; or two or more thereof, to the subject to determine the level of expression of COX-2 protein in the cells of the breast cancer, lung cancer, prostate cancer, colon cancer, liver cancer or melanoma compared to a control, the level of expression of COX-2 nucleic acid in the cells of the breast cancer, lung cancer, prostate cancer, colon cancer, liver cancer or melanoma compared to a control, the level of activity of COX-2 in the cells of the breast cancer, lung cancer, prostate cancer, colon cancer, liver cancer or melanoma compared to a control and/or the level of activity of Akt in the cells of the breast cancer, lung cancer, prostate cancer, colon cancer, liver cancer or melanoma compared to a control.

Methods of treating a subject having or suspected of having cancer according to aspects of the present invention include assaying COX-2 protein, COX-2 nucleic acid, COX-2 activity and/or Akt3 activity in cells of the cancer prior to and/or after administration of a pharmaceutical composition including a selenium-containing COX-2 inhibitor to the subject to determine the level of expression of COX-2 protein in the cells of the cancer compared to a control, the level of expression of COX-2 nucleic acid in the cells of the cancer compared to a control, the level of activity of COX-2 in the cells of the cancer compared to a control and/or the level of activity of Akt3 in the cells of the cancer compared to a control.

Methods of treating a subject having or suspected of having cancer according to aspects of the present invention include assaying COX-2 protein, COX-2 nucleic acid, COX-2 activity and/or Akt3 activity in cells of the cancer prior to and/or after administration of a pharmaceutical composition including selenocoxib-1-GSH, selenocoxib-1-cysteine or selenocoxib-1-NAC; or two or more thereof, to the subject to determine the level of expression of COX-2 protein in the cells of the cancer compared to a control, the level of expression of COX-2 nucleic acid in the cells of the cancer compared to a control, the level of activity of COX-2 in the cells of the cancer compared to a control and/or the level of activity of Akt3 in the cells of the cancer compared to a control.

Methods of treating a subject having or suspected of having breast cancer, lung cancer, prostate cancer, colon cancer, liver cancer or melanoma according to aspects of the present invention include assaying COX-2 protein, COX-2 nucleic acid, COX-2 activity and/or Akt3 activity in cells of the breast cancer, lung cancer, prostate cancer, colon cancer, liver cancer or melanoma prior to and/or after administration of a pharmaceutical composition including a selenium-containing COX-2 inhibitor to the subject to determine the level of expression of COX-2 protein in the cells of the breast cancer, lung cancer, prostate cancer, colon cancer, liver cancer or melanoma compared to a control, the level of expression of COX-2 nucleic acid in the cells of the breast cancer, lung cancer, prostate cancer, colon cancer, liver cancer or melanoma compared to a control, the level of activity of COX-2 in the cells of the breast cancer, lung cancer, prostate cancer, colon cancer, liver cancer or melanoma compared to a control and/or the level of activity of Akt3 in the cells of the breast cancer, lung cancer, prostate cancer, colon cancer, liver cancer or melanoma compared to a control.

Methods of treating a subject having or suspected of having breast cancer, lung cancer, prostate cancer, colon cancer, liver cancer or melanoma according to aspects of the present invention include assaying COX-2 protein, COX-2 nucleic acid, COX-2 activity and/or Akt3 activity in cells of the breast cancer, lung cancer, prostate cancer, colon cancer, liver cancer or melanoma prior to and/or after administration of a pharmaceutical composition including selenocoxib-1-GSH, selenocoxib-1-cysteine or selenocoxib-1-NAC; or two or more thereof to the subject to determine the level of expression of COX-2 protein in the cells of the breast cancer, lung cancer, prostate cancer, colon cancer, liver cancer or melanoma compared to a control, the level of expression of COX-2 nucleic acid in the cells of the breast cancer, lung cancer, prostate cancer, colon cancer, liver cancer or melanoma compared to a control, the level of activity of COX-2 in the cells of the breast cancer, lung cancer, prostate cancer, colon cancer, liver cancer or melanoma compared to a control and/or the level of activity of Akt3 in the cells of the breast cancer, lung cancer, prostate cancer, colon cancer, liver cancer or melanoma compared to a control.

Optionally, the control is a result of assaying a test sample including cells of the cancer obtained from the subject prior to administration of the pharmaceutical composition.

In a further option, an adjunct anti-cancer treatment is also administered to the subject according to aspects of methods of the present invention.

Optionally, the pharmaceutical composition is administered topically.

In a further option, an additional therapeutic agent is administered to the subject.

Methods of treating melanoma in a subject are provided according to aspects of the present invention which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a subject are provided according to aspects of the present invention which include administering a therapeutically effective amount of selenocoxib-1-GSH, selenocoxib-1-cysteine or selenocoxib-1-

NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention which include administering a therapeutically effective amount of selenocoxib-1-GSH, selenocoxib-1-cysteine or selenocoxib-1-NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a subject are provided according to aspects of the present invention, wherein the subject has or is suspected of having melanoma characterized by increased COX-2 protein or nucleic acid, increased COX-2 activity and/or increased Akt activity compared to a control, which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a subject are provided according to aspects of the present invention, wherein the subject has or is suspected of having melanoma characterized by increased COX-2 protein or nucleic acid, increased COX-2 activity and/or increased Akt activity compared to a control, which include administering a therapeutically effective amount of selenocoxib-1-GSH, selenocoxib-1-cysteine or selenocoxib-1-NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention, wherein the subject has or is suspected of having melanoma characterized by increased COX-2 protein or nucleic acid, increased COX-2 activity and/or increased Akt activity compared to a control, which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention, wherein the subject has or is suspected of having melanoma characterized by increased COX-2 protein or nucleic acid, increased COX-2 activity and/or increased Akt activity compared to a control, which include administering a therapeutically effective amount of selenocoxib-1-GSH, selenocoxib-1-cysteine or selenocoxib-1-NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a subject are provided according to aspects of the present invention, wherein the subject has or is suspected of having melanoma characterized by increased COX-2 protein or nucleic acid, increased COX-2 activity and/or increased Akt3 activity compared to a control, which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a subject are provided according to aspects of the present invention, wherein the subject has or is suspected of having melanoma characterized by increased COX-2 protein or nucleic acid, increased COX-2 activity and/or increased Akt3 activity compared to a control, which include administering a therapeutically effective amount of selenocoxib-1-GSH, selenocoxib-1-cysteine or selenocoxib-1-NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention, wherein the subject has or is suspected of having melanoma characterized by increased COX-2 protein or nucleic acid, increased COX-2 activity and/or increased Akt3 activity compared to a control, which include administering a therapeutically effective amount of a pharmaceutical composition including a selenium-containing COX-2 inhibitor. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

Methods of treating melanoma in a human subject are provided according to aspects of the present invention, wherein the subject has or is suspected of having melanoma characterized by increased COX-2 protein or nucleic acid, increased COX-2 activity and/or increased Akt3 activity compared to a control, which include administering a therapeutically effective amount of selenocoxib-1-GSH, selenocoxib-1-cysteine or selenocoxib-1-NAC; or two or more thereof. Optionally, the pharmaceutical composition is formulated for topical application. In a further option, the pharmaceutical composition includes a particulate or nanoparticulate pharmaceutically acceptable carrier. In another option, the pharmaceutical composition includes nanoliposomes having an average particle size in the range of 1-100 nm. In a further option, an additional therapeutic agent is included in the pharmaceutical composition. Another option is administration of an adjunct anti-cancer treatment to the subject. In a still further option, the pharmaceutical composition is administered topically.

According to aspects of the present invention, administering the therapeutically effective amount of the pharmaceutical composition to the subject detectably increases apoptosis and/or decreases proliferation of cells of the melanoma and has negligible effect on non-cancer cells.

According to aspects of the present invention, administering the therapeutically effective amount of the pharmaceutical composition to the subject detectably decreases free radicals and/or reactive oxygen species of cells of the melanoma and has negligible effect on non-cancer cells.

Methods of treating a subject having or suspected of having melanoma according to aspects of the present invention include assaying COX-2 protein, COX-2 nucleic acid, COX-2 activity and/or Akt activity in cells of the melanoma, prior to and/or after administration of a pharmaceutical composition including a selenium-containing COX-2 inhibitor to the subject, to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt in the cells of the melanoma compared to a control.

Methods of treating a subject having or suspected of having melanoma according to aspects of the present invention include assaying COX-2 protein, COX-2 nucleic acid, COX-2 activity and/or Akt activity in cells of the melanoma prior to and/or after administration of a pharmaceutical composition including selenocoxib-1-GSH, selenocoxib-1-cysteine or selenocoxib-1-NAC; or two or more thereof, to the subject to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt in the cells of the melanoma compared to a control.

Methods of treating a subject having or suspected of having melanoma according to aspects of the present invention include assaying COX-2 protein, COX-2 nucleic acid, COX-2 activity and/or Akt3 activity in cells of the melanoma prior to and/or after administration of a pharmaceutical composition including a selenium-containing COX-2 inhibitor to the subject to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt3 in the cells of the melanoma compared to a control.

Methods of treating a subject having or suspected of having melanoma according to aspects of the present invention include assaying COX-2 protein, COX-2 nucleic acid, COX-2 activity and/or Akt3 activity in cells of the melanoma prior to and/or after administration of a pharmaceutical composition including selenocoxib-1-GSH, selenocoxib-1-cysteine or selenocoxib-1-NAC; or two or more thereof, to the subject to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt3 in the cells of the melanoma compared to a control.

According to aspects of the present invention, assay of COX-2 protein, COX-2 nucleic acid, COX-2 activity and/or Akt3 activity in cells of the melanoma is performed after administration of the pharmaceutical composition including a selenium-containing COX-2 inhibitor to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt3 in the cells of the melanoma compared to a test sample obtained from the subject prior to administration of the pharmaceutical composition. Optionally, the control is a result of assaying a test sample including cells of the melanoma obtained from the subject prior to administration of the pharmaceutical composition.

According to aspects of the present invention, assay of COX-2 protein, COX-2 nucleic acid, COX-2 activity and/or Akt3 activity in cells of the melanoma is performed after administration of the pharmaceutical composition including selenocoxib-1-GSH, selenocoxib-1-cysteine or selenocoxib-1-NAC; or two or more thereof, to determine the level of expression of COX-2 protein in the cells of the melanoma compared to a control, the level of expression of COX-2 nucleic acid in the cells of the melanoma compared to a control, the level of activity of COX-2 in the cells of the melanoma compared to a control and/or the level of activity of Akt3 in the cells of the melanoma compared to a test sample obtained from the subject prior to administration of the pharmaceutical composition. Optionally, the control is a result of assaying a test sample including cells of the melanoma obtained from the subject prior to administration of the pharmaceutical composition.

DETAILED DESCRIPTION OF THE INVENTION

Figure 1A:
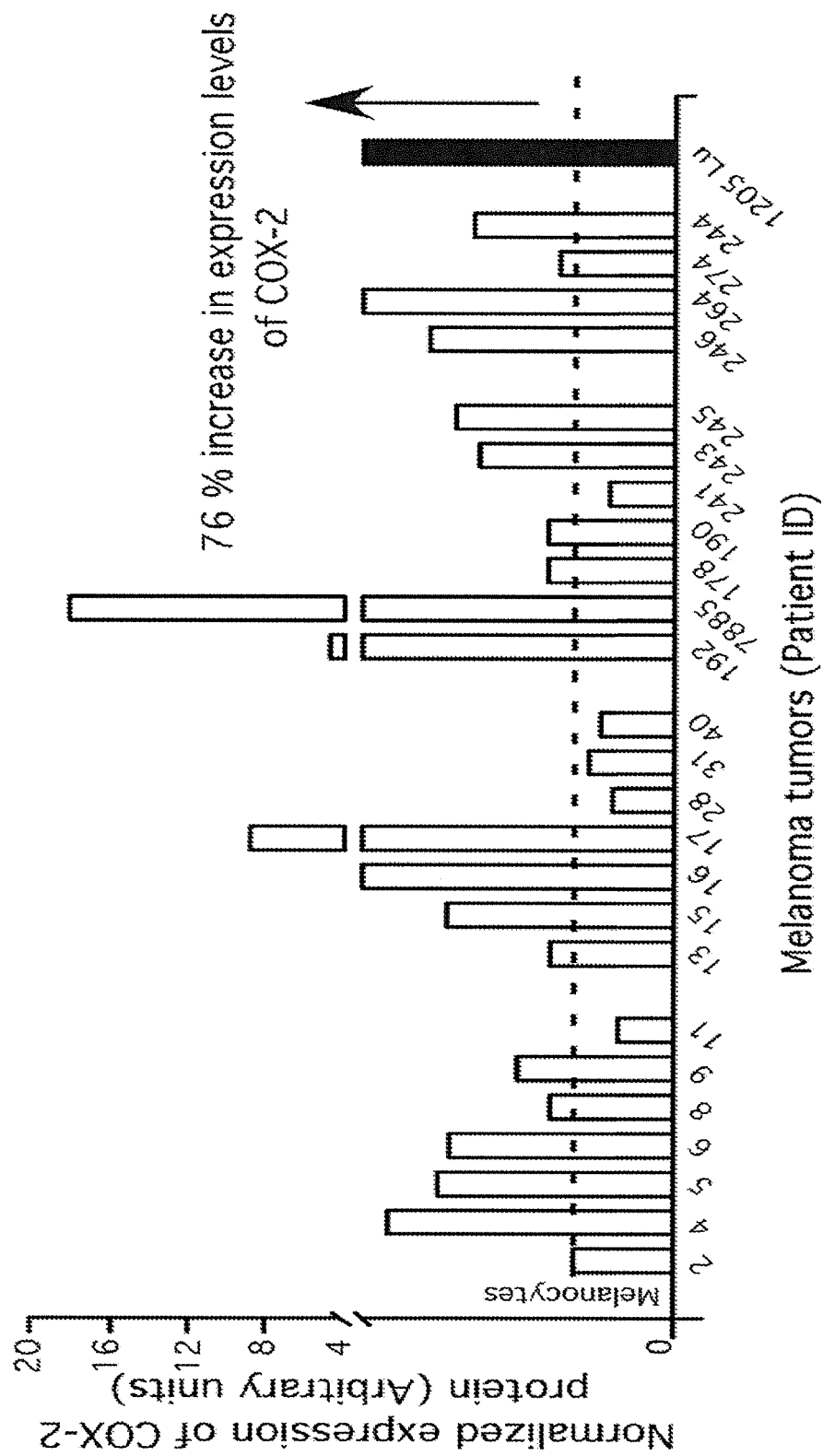
FIG. 1A is a graph showing elevated levels of COX-2 expression in melanoma patient tumors and cell lines.

Compositions and methods are provided by the present invention to inhibit COX-2 activity in cancer cells, reduce survival and/or reduce proliferation of cancer cells.

The singular terms "a," "an," and "the" used herein include plural referents unless the context clearly indicates otherwise.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

Anti-cancer compositions and methods are provided according to aspects of the present invention. According to aspects of the present invention, the present invention relates to inventive selenium-containing COX-2 inhibitors, methods for treatment and/or prevention of cancer in a subject using one or more selenium-containing COX-2 inhibitors.

According to aspects of the present invention, a selenium-containing COX-2 inhibitor compound included in methods and compositions of the invention is selenocoxib-1-glutathione (selenocoxib-1-GSH), selenocoxib-1-cysteine and/or selenocoxib-1-N-aceylcysteine (selenocoxib-1-NAC).

Selenocoxib-1-GSH has the structural formula:

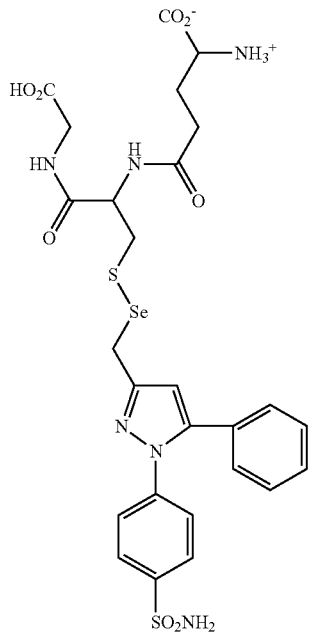

2-amino-4-(1-{carboxymethyl-carbamoyl)-2-[5-phenyl-1-(4-sulfamoylphenyl)-1H-pyrazol-3yl)methylselanylthiol-ethylcarbamoyl}-butyric acid.

Selenocoxib-1-cysteine has the structural formula:

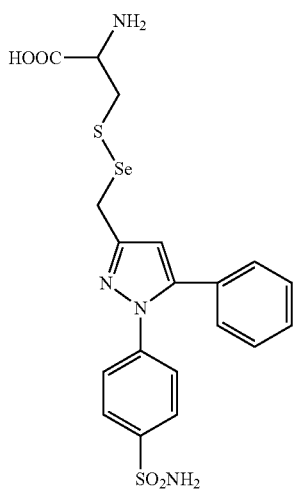 [SMILES: NC(CS[Se]Cc1cc(-c2ccccc2)n(-c2ccc(S(N)(=O)=O)cc2)n1)C(=O)O]

Selenocoxib-1-N-aceylcysteine has the structural formula:

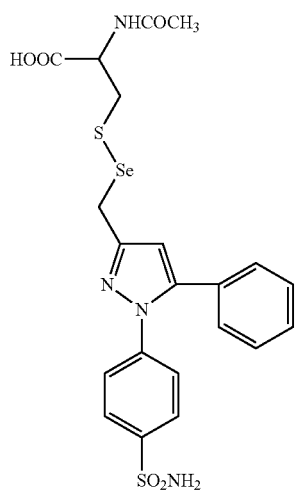

Compositions and methods according to aspects of the present invention prevent and inhibit cancer cell proliferation and tumor development and are considered useful as chemotherapeutic and chemopreventive agents.

Methods and compositions are provided according to the present invention for treating cancer. Particular cancers treated using methods and compositions described herein are characterized by abnormal cell proliferation including, but not limited to, pre-neoplastic hyperproliferation, cancer in-situ, neoplasms, metastases, tumors, benign growths or other abnormal cell proliferation condition responsive to a composition of the present invention. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of a composition of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to a composition of the present invention, a therapeutically effective amount of a composition of the present invention is effective to ameliorate or prevent one or more signs and/or symptoms of the condition. For example, a therapeutically effective amount of a composition of the present invention is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other abnormal cell proliferation condition responsive to a composition of the present invention, without significant effect to increase apoptosis or decrease proliferation of non-cancer cells.

In particular aspects, cancers treated using methods and compositions of the present invention are characterized by elevated expression and/or activity of COX-2. Elevated expression and/or activity of COX-2 has been reported in cancers of the prostate, breast, colon, kidney, liver and melanocyte, Ghosh N et al., Pharmacol Rep, 2010; 62:233-44; Becker M R et al., Melanoma Res, 2009; 19:8-16; and Flockhart R J et al., Br J Cancer, 2009; 101:1448-55. Treatment of a cancer characterized by elevated expression and/or activity of COX-2 using methods and compositions of the present invention results in a detectable decrease in expression and/or activity of COX-2. Assays for expression and/or activity of COX-2 which identify cancers amenable to treatment according to the present invention and which allow for monitoring of effectiveness of treatment include, but are not limited to immunoassays, nucleic acid assays and enzyme activity assays.

The term "expression" refers to transcription of a gene to produce a corresponding mRNA and/or translation of the mRNA to produce the corresponding protein.

In particular aspects, cancers treated using methods and compositions of the present invention are characterized by Akt dysregulation.

Akt, a serine/threonine protein kinase also known as protein kinase B, has a stimulatory effect on cell cycle progression, cell proliferation and inhibition of apoptosis. Akt proteins, nucleic acids and signaling pathway components are described, for instance, see Testa, J. R. et al., PNAS, 98:10983-10985; Fayard, E. et al., J. Cell Sci., 118:5675-5678, 2005; Cheng, J. and S. Nicosia, (2001) AKT signal transduction pathway in oncogenesis, in Encyclopedic Reference of Cancer, D. Schwab, Editor. 2001, Springer: Berlin, Germany, p. 35-7; Datta, S. R., et al. (1999) Cellular survival: a play in three Akts. Genes Dev, 13(22): 2905-27; Fayard, E. et al. (2005) J Cell Sci, 118(Pt 24: 5675-8; Mirza, A. M., Fayard, E. et al. (2000) 2000. 11(6: 279-92; Nicholson, K. M. and N. G. Anderson, (2002) Cell Signal, 2002, 14(5): p. 381-95; Paez, J. and W. Sellers, (2003) P13K/PTEN/Akt Pathway: A Critical Mediator of Oncogenic Signaling, in Signal Transduction in Cancer, D. Frank, Editor. 2003, Kluwer Academic Publishers: Netherlands; and Testa, J. R.; P. N. Tsichlis, (2005) Oncogene, 24(50): 7391-3 and other references listed herein.

Akt family members, Akt1, Akt2 and Akt3, are activated by phosphorylation, membrane translocation, increases in gene copy number and/or loss of a negative regulatory phosphatase, PTEN. Increased activation of Akt, including increased levels of Akt and/or increased levels of phosphorylated Akt is an indicator of Akt dysregulation associated with proliferation and cell survival in pathogenic conditions, such as cancer.

Akt3 is active in ~70% of melanomas. While all three Akt isoforms are expressed in melanocytes and melanoma cells, Akt3 is the predominantly active family member. Dysregulated Akt3 activity in melanoma cells reduces cellular apoptosis mediated through caspase-3, thereby promoting melanoma tumor development.

Treatment of a cancer characterized by dysregulation of Akt using methods and compositions of the present invention results in a detectable decrease in expression and/or activity of Akt. In particular, treatment of a cancer characterized by dysregulation of Akt3 using methods and compositions of the present invention results in a detectable decrease in expression and/or activity of Akt3. Akt dysregulation is determined, for instance, by measurement of Akt gene copy number, Akt protein or RNA levels and/or levels of phosphorylated Akt, in cells known or suspected to be dysplasic, pre-cancerous, cancerous, metastatic or otherwise characterized by abnormal cell proliferation compared to normal cells. Assays for Akt dysregulation which identify cancers amenable to treatment according to the present invention and which allow for monitoring of effectiveness of treatment include, but are not limited to immunoassays and nucleic acid assays.

Methods of treating a subject are provided according to aspects of the present invention which include administering a therapeutically effective amount of an inventive selenium-containing COX-2 inhibitor compound wherein the subject has a condition characterized by Akt dysregulation and/or elevated expression and/or activity of COX-2, such as cancer, pre-neoplastic hyperproliferation, cancer in-situ, neoplasms, metastasis, tumor or benign growth. In certain aspects of methods of treatment of a subject, contacting cells characterized by Akt dysregulation with a therapeutic amount of an inventive selenium-containing COX-2 inhibitor compound decreases a component of an Akt signaling pathway selected from the group consisting of: an Akt1 signaling pathway; an Akt2 signaling pathway; an Akt3 signaling pathway; and a combination thereof. For example, contacting the cell with an inventive selenium-containing COX-2 inhibitor compound decreases a component of an Akt signaling pathway selected from pAkt1, pAkt2, pAk3, pPRAS40 and a combination thereof.

Since selecoxib-1-GSH, and other inventive selenium-containing COX-2 inhibitor compounds of the present invention, targets COX-2 and Akt signaling in melanoma cells and other cancer types, expression or activity of these proteins or any downstream member of these signaling cascades could be used to identify patients that could be treated with selecoxib-1-GSH, and other inventive selenium-containing COX-2 inhibitor compounds of the present invention, or to measure the therapeutic efficacy thereof. For example, in melanoma the expression or activity of Akt3 or downstream PRAS40 would be measured, prior to and/or following treatment with selecoxib-1-GSH, and other inventive selenium-containing COX-2 inhibitor compounds of the present invention. Other downstream members of these pathways could be assessed in a similar fashion.

In addition to direct measurement of protein levels and/or activity of COX-2, Akt1, Akt2, Akt3, pAkt1, pAkt2 and/or pAkt3, one or more downstream components of the signaling pathways of these can be measured.

In aspects of described methods, treatment of a subject with a therapeutically effective amount an inventive selenium-containing COX-2 inhibitor compound is substantially without toxic effect on cells in which Akt is not dysregulated and cells without elevated expression and/or activity of COX-2.

Methods of treating a subject are provided according to aspects of the present invention which include administering a therapeutically effective amount of a selenium-containing COX-2 inhibitor and wherein the subject has a condition characterized by Akt dysregulation and/or elevated expression and/or activity of COX-2, such as cancer, pre-neoplastic hyperproliferation, cancer in-situ, neoplasms, metastasis, tumor or benign growth.

In particular aspects, cancers treated using methods and compositions of the present invention are characterized by Akt dysregulation, elevated COX-2 expression and/or elevated activity of COX-2, including, but not limited to, breast cancer, lung cancer, prostate cancer, colon cancer, liver cancer and melanoma. Akt dysregulation, elevated COX-2 expression and/or elevated activity of COX-2 can be detected by assaying a sample, such as a biopsy sample, obtained from a subject having or suspected of having cancer.

Aspects of the present invention include assaying one or more of COX-2, Akt1, Akt2, Akt3, pAkt1 (phosphorylated Akt1), pAkt2 (phosphorylated Akt2) and pAkt3 (phosphorylated Akt3) protein in a test sample obtained from a subject having or suspected of having cancer.

In addition to direct measurement of expression and/or activity of COX-2, Akt1, Akt2, Akt3, pAkt1, pAkt2 and/or pAkt3, one or more downstream components of the signaling pathways of these can be measured.

Phosphorylation of the downstream Akt3 substrate PRAS40 is significantly inhibited by treatment of a cancer with a selenium-containing COX-2 inhibitor of the present invention. For example, phosphorylation of the downstream Akt3 substrate PRAS40 is significantly inhibited by treatment of a cancer with selenocoxib-1-GSH of the present invention.

Aspects of the present invention include assaying one or more of COX-2, Akt1, Akt2, Akt3, pAkt1, pAkt2 and pAkt3 protein in a test sample obtained from a subject having or suspected of having melanoma.

Aspects of the present invention include assaying one or more of COX-2, Akt3, and pAkt3 proteins in a test sample obtained from a subject having or suspected of having melanoma.

Aspects of the present invention include assaying one or more of COX-2, Akt1, Akt2 and Akt3 nucleic acids in a test sample obtained from a subject having or suspected of having cancer.

Aspects of the present invention include assaying one or more of COX-2, Akt1, Akt2 and Akt3 nucleic acids in a test sample obtained from a subject having or suspected of having melanoma.

A test sample can be any biological fluid, cell or tissue of a subject containing or suspected of containing cancer cells, illustratively including blood, plasma, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid, synovial fluid, bone marrow aspirate, tumor cells or tissue, organ cells or tissue, such as biopsy material.

Immunoassay methods can be used to assay any one or more proteins such as COX-2, Akt1, Akt2, Akt3, pAkt1, pAkt2 and pAkt3 in a sample. Immunoassays that can be used include but are not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. A method to assay one or more proteins such as COX-2, Akt1, Akt2, Akt3, pAkt1, pAkt2 and pAkt3 is to isolate circulating tumor cells and probe the fixed cells with quantum dots or similar imaging moieties conjugated to antibodies thereby measuring levels of COX-2 protein or the presence of pAKT in the cells, allowing for simultaneous measurement of the levels of two or more proteins in the same cell. Comparison to normal control cells is performed to assess tumor status and/or drug efficacy.

Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: First Principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Antibodies directed against COX-2, Akt1, Akt2, Akt3, pAkt1, pAkt2 or pAkt3 can be polyclonal or monoclonal antibodies. Suitable antibodies also include chimeric antibodies, humanized antibodies, and protein binding antibody fragments and molecules having specific protein binding functionality, such as aptamers. Examples of antibody fragments that can be used in embodiments of inventive assays include Fab fragments, Fab' fragments, F(ab'), fragments, Fd fragments, Fv fragments, scFv fragments, and domain antibodies (dAb).

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

Aptamers can be used to assay a sample for proteins such as COX-2, Akt1, Akt2, Akt3, pAkt1, pAkt2 and/or pAkt3. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Optionally, spectrometric analysis is used to assay a sample for proteins such as COX-2, Akt1, Akt2, Akt3, pAkt1, pAkt2 and/or pAkt3. For example mass analysis can be used in an assay according to embodiments of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Assay of proteins such as COX-2, Akt1, Akt2, Akt3, pAkt1, pAkt2 and/or pAkt3 can be performed on cells and tissues.

One or more standards can be used to allow quantitative determination of proteins such as COX-2, Akt1, Akt2, Akt3, pAkt1, pAkt2 and/or pAkt3 in a sample.

Assay of proteins such as COX-2, Akt1, Akt2, Akt3, pAkt1, pAkt2 and/or pAkt3 in a test sample is optionally compared to assay of the same protein in a control sample. Control samples may be obtained from one or more normal subjects, for example.

According to embodiments of the present invention, assays for COX-2, Akt1, Akt2, Akt3, pAkt1 pAkt2 and/or pAkt3 are used to monitor disease progression and/or effectiveness of treatment of a subject. Thus, for example, a test sample is obtained from the subject before treatment of cancer and at one or more times during and/or following treatment in order to assess effectiveness of the treatment. In a further example, a test sample is obtained from the subject at various times in order to assess the course or progress of disease or healing.

An assay according to embodiments of the present invention detects COX-2, Akt1, Akt2, and/or Akt3 nucleic acid in a test sample of a subject known to have cancer, suspected of having a particular disease or injury or at risk of having a particular disease or injury.

Assays for detecting COX-2, Akt1, Akt2, and/or Akt3 nucleic acid, particularly mRNA or cDNA, include, but are not limited to, polymerase chain reactions (PCR) such as RT-PCR, dot blot, in situ hybridization, Northern blot and RNase protection.

COX-2 activity can be determined using a COX-2 enzyme activity assay. COX-2 activity can be measured using any of various assays such as a commercially available fluorometric assay for COX-1 (cyclooxygenase-1) and COX-2 isozymes using the peroxide-sensitive dye AMPLEX Red reagent, 10-acetyl-3,7-dihydroxyphenoxazine. Activity of both COX-1 and COX-2 to oxidize 10-acetyl-3,7-dihydroxyphenoxazine in the presence of arachidonic acid, producing the highly fluorescent dye resorufin allows for detection of both COX-1 and COX-2 isozymes and use of selective inhibitors of COX-1 or COX-2 allows determination of the activity of each enzyme individually. Selective inhibitors of COX-2 are well known and include, for example, celecoxib. Selective inhibitors of COX-1 are well known and include, for example aspirin, FR122047, mofezolac, P6, SC-560 and TFAP.

A test sample from a subject is optionally purified for assay according to a method of the present invention. The term "purified" in the context of a test sample refers to separation of COX-2, Akt1, Akt2, Akt3, pAkt1, pAkt2 and/or pAkt3 and/or a nucleic acid encoding COX-2, Akt1, Akt2, and/or Akt3 from at least one other component present in the test sample. Test sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography. Details of these and other techniques for nucleic acid assay are known in the art, for example, as described in J. Sambrook and D. W. Russell, Molecular Cloning: A Laboratory Manual, Cold Spring Harbor Laboratory Press, 3rd Ed., 2001; and F. M. Ausubel, Ed., Short Protocols in Molecular Biology, Current Protocols; 5th Ed., 2002.

A method of treating a subject is provided according to aspects of the present invention which includes administering to a subject in need thereof a therapeutically effective amount of one or more selenium-containing COX-2 inhibitors.

According to aspects of the invention, a method of treating a subject includes administering an effective amount of selenocoxib-1-GSH.

According to aspects of the invention, a method of treating a subject includes administering an effective amount of selenocoxib-1-cysteine.

According to aspects of the invention, a method of treating a subject, includes administering an effective amount of selenocoxib-1-N-aceylcysteine.

According to aspects, two or more selenium-containing COX-2 inhibitors are administered to a subject in need thereof. The two or more selenium-containing COX-2 inhibitors can be administered (1) as a pharmaceutical composition that includes the two or more selenium-containing COX-2 inhibitors of the present invention together; and/or (2) by co-administration of the two or more selenium-containing COX-2 inhibitors of the present invention where the selenium-containing COX-2 inhibitors have not been formulated in the same composition. When using separate formulations, the two or more selenium-containing COX-2 inhibitors of the present invention may be administered at the same time, intermittent times, staggered times, prior to, subsequent to, or combinations thereof.

According to aspects of the invention, an administered selenium-containing COX-2 inhibitor is a pharmaceutically acceptable salt, ester, amide, solvate or stereoisomer of a selenium-containing COX-2 inhibitor.

According to aspects of the invention, an administered selenium-containing COX-2 inhibitor is a pharmaceutically acceptable salt, ester, amide, solvate or stereoisomer of selenocoxib-1-GSH.

According to aspects of the invention, an administered selenium-containing COX-2 inhibitor is a pharmaceutically acceptable salt, ester, amide, solvate or stereoisomer of selenocoxib-1-cysteine or selenocoxib-1-N-acetylcysteine.

A "pharmaceutically acceptable" salt, ester, amide or solvate is suitable for use in a subject without undue toxicity or irritation to the subject and is effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N, N'-dibenzylethylenediamine, ethanolamine, ethylamine, ethylenediamine, glucosamine, histidine, hydrabamine, isopropylamine, 1H-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Pharmaceutically acceptable solvates illustratively include hydrates, ethanolates, methanolates.

Exemplary pharmaceutically acceptable amides include amides derived from ammonia, primary C1-C6 alkyl amines and secondary C1-C6 dialkyl amines including those in the form of a 5- or 6-member nitrogen-containing heterocycle.

Compositions including a selenium-containing COX-2 inhibitor are provided according to aspects of the present invention which inhibit tumor growth by inhibiting an Akt signaling cascade and/or inhibiting COX-2 in cells characterized by Akt dysregulation and/or elevated COX-2 expression and/or elevated COX-2 activity.

Methods including administration of one or more selenium-containing COX-2 inhibitors to a subject in need thereof are provided according to particular aspects of the present invention which have utility, for example, in inhibiting the Akt signaling cascade and/or COX-2 in cancer cells.

Methods including administration of one or more selenium-containing COX-2 inhibitors to a subject in need thereof are provided according to particular aspects of the present invention which have utility, for example, in decreasing levels of free radicals and/or reactive oxygen species (ROS) in cancer cells. ROS can be measured by methods including but not limited to using an indicator such as 2', 7'-dichlorfluorescein or dichlorodihydrofluorescein diacetate as described herein.

Inhibitors of the Akt signaling cascade and/or COX-2 according to aspects of the present invention have utility in treatment of subject having cancer or at risk of having cancer in which Akt deregulation and/or elevated expression and/or activity of COX-2 occurs, such as in melanoma and other cancers including, but not limited to, cancers of the prostate, breast, colon, kidney, lung and liver.

Methods of modulating an Akt protein, such as an Akt1, Akt2 and/or an Akt3 protein, in a cell are provided according to aspects of the present invention which include contacting the cell with an effective amount of a selenium-containing COX-2 inhibitor.

Pharmaceutical compositions including a selenium-containing COX-2 inhibitor of the present invention are provided according to aspects of the present invention.

A pharmaceutical composition includes a selenium-containing COX-2 inhibitor of the present invention and a pharmaceutically acceptable carrier according to aspects of the present invention. The term "pharmaceutically acceptable carrier" refers to a carrier which is substantially non-toxic to a subject to which the composition is administered and which is substantially chemically inert with respect to a selenium-containing COX-2 inhibitor of the present invention.

A pharmaceutical composition according to the invention generally includes about 0.1-99% of a selenium-containing COX-2 inhibitor. Combinations of selenium-containing COX-2 inhibitors in a pharmaceutical composition are also considered within the scope of the present invention.

Combination Treatments

Combinations of therapeutic agents are administered according to aspects of the present invention. In some aspects, two or more selenium-containing COX-2 inhibitors of the present invention are administered to a subject to treat cancer in a subject in need thereof. In further aspects, at least one selenium-containing COX-2 inhibitor of the present invention and at least one additional therapeutic agent are administered to a subject to treat cancer in a subject in need thereof. In still further aspects, at least one selenium-containing COX-2 inhibitor of the present invention and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing one or more selenium-containing COX-2 inhibitors of the present invention and one or more additional therapeutic agents may show synergistic effects, e.g., a greater therapeutic effect than would be observed using either the one or more selenium-containing COX-2 inhibitors of the present invention or one or more additional therapeutic agents alone as a monotherapy.

According to aspects, combination therapies include: (1) pharmaceutical compositions that include one or more selenium-containing COX-2 inhibitors of the present invention in combination with one or more additional therapeutic agents; and (2) co-administration of one or more selenium-containing COX-2 inhibitors of the present invention with one or more additional therapeutic agents wherein the one or more selenium-containing COX-2 inhibitors of the present invention and the one or more additional therapeutic agents have not been formulated in the same composition. When using separate formulations, the one or more selenium-containing COX-2 inhibitors of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the one or more selenium-containing COX-2 inhibitors of the present invention and the one or more additional therapeutic agents used in methods of the present invention. Synergistic effects of combination treatments including a selenium-containing COX-2 inhibitor of the present invention may be obtained.

In particular aspects of the present invention, synergistic anti-cancer effects of combination treatments including administration of selenocoxib-1-GSH and administration of plumbagin, also known as 5-hydroxy-2-methyl-1,4-naphthoquinone, may be obtained.

In particular aspects of the present invention, synergistic anti-cancer effects of a combination treatment of a subject having or suspected of having melanoma including administration of selenocoxib-1-GSH and administration of plumbagin may be obtained.

In particular aspects of the present invention, synergistic anti-cancer effects of a combination treatment of a subject having or suspected of having a cancer characterized by increased COX-2 protein or nucleic acid, increased COX-2 activity and/or increased Akt activity including administration of selenocoxib-1-GSH and administration of plumbagin may be obtained.

In particular aspects of the present invention, synergistic anti-cancer effects of a combination treatment of a subject having or suspected of having melanoma including administration of selenocoxib-1-GSH and administration of plumbagin may be obtained.

In particular aspects synergistic effects of combination treatments including administration of a nanoparticulate liposomal formulation of selenocoxib-1-GSH and administration of a nanoparticulate liposomal formulation of an additional anti-cancer agent may be obtained.

According to particular aspects of the present invention, synergistic effects of combination treatments including administration of a nanoparticulate liposomal formulation of selenocoxib-1-GSH and administration of a nanoparticulate liposomal formulation of plumbagin may be obtained.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include 5-hydroxy-2-methyl-1,4-naphthoquinone (plumbagin), acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more selenium-containing COX-2 inhibitors described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to a selenium-containing COX-2 inhibitor, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular aspects, compositions of the present invention are formulated for topical application. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansel's Pharmaceutical Dosage Forms and Drug Delivery Systems, $8^{th}$ Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, Pa., 2006; and Allen, L. V. et al., Ansel's Pharmaceutical Dosage Forms and Drug Delivery Systems, 8 Ed., Lippincott, Williams & Wilkins, Philadelphia, Pa., 2005.

The term subject refers to an individual in need of treatment for a pathological condition, particularly cancer, and generally includes mammals and birds, such as, but not limited to, humans, other primates, cats, dogs, cows, horses, rodents, pigs, sheep, goats and poultry.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds—hours. In a further aspect, administration may include multiple doses administered over a period of days—years, such as for chronic treatment of cancer.

With regard to administration of a particular inventive composition to a mammalian subject, particular exemplary effective dosage ranges without significant systemic toxicity are described in terms of amounts of selenium administered via administration of the inventive composition. Thus, for example, when delivered by a parenteral route, such as intraperitoneal or intravenous, an exemplary therapeutically effective dosage of an inventive composition is in the range of about 1-4 ppm selenium, administered three times per week. It is noted that the dose range "about 1-4 ppm selenium" refers to a dose of "about 1 mg/kg-10 mg/kg of selenium," depending on the particular compound administered.

In a further example, when delivered topically, an exemplary therapeutically effective dosage of a selenium-containing COX-2 inhibitor described herein is in the range of about 0.1-2 ppm selenium, administered daily. In one example, topically administered selenocoxib-1-GSH, selenocoxib-1-cysteine and/or selenocoxib-1-NAC is given at a dose of 1.5 ppm selenium (equivalent to 5.12 mg/kg body weight) every day.

In a further example, when delivered orally, an exemplary therapeutically effective dosage of a selenium containing compound described herein is in the range of about 1-15 ppm selenium. In a particular example, an oral dose in the range of 1-15 ppm of selenium equivalent to 3.412 mg/kg-51.18 mg/kg body weight of selenocoxib-1-GSH is a therapeutically effective dose.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Advantageously, selenium-containing COX-2 inhibitors according to aspects of the present invention are formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is a nanoparticulate carrier formulated such that particles have an average particle size in the range of about 1 nm-100 nm.

Selenium-containing COX-2 inhibitor compositions of the present invention optionally include a lipid-based carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions, kits and methods according to aspects of the invention. The term "liposome" refers to a bilayer particle of amphipathic lipid molecules enclosing an aqueous interior space. Liposomes are typically produced as small unilamellar vesicles (SUVs), large unilamellar vesicles (LUVs) or multilammellar vesicles (MLVs). A selenium-containing COX-2 inhibitor composition of the present invention is associated with liposomes by encapsulation in the aqueous interior space of the liposomes, disposed in the lipid bilayer of the liposomes and/or associated with the liposomes by binding, such as ionic binding or association by van der Waals forces. Thus, selenium-containing COX-2 inhibitor composition of the present invention is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer-1 micron in diameter although they are not limited with regard to size. A particulate carrier is typically formulated such that particles have an average particle size in the range of about 1 nm-10 microns. In particular aspects, a particulate carrier is a nanoparticulate carrier formulated such that particles have an average particle size in the range of about 1 nm-100 nm.

Liposomal formulations of selenium-containing COX-2 inhibitor compositions according to aspects of the present invention include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy)propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyri styloxypropyl)(dimethyl)(hydroxyethyl)ammonium (DMRIE); dioctadecyldimethylammonium chloride (DODAC), Dimethyldidodecylammonium bromide (DDAB); 3β[N-(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Di-oleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoyl-phosphatidylethanolamine (DOPE), distearoylphosphatidy-lethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoyl-phosphatidyl glycerol, dioleoylphosphatidyl glycerol, dilauryloylphosphatidyl glycerol, dipahnitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000] (DPPE-PEG-2000), and polyethyleneglycol 750 octadecylsphingosine (PEG (750) C8).

Exemplary ratios of components included in liposomal formulations of the present invention are neutral lipid: polyethyleneglycol modified neutral lipid—80:20 mol %.

For example, liposomal formulations include L-alpha-phosphatidylcholine and 1,2-dipalmitoyl-sn-glycero-3-phosphoethanolamine-N-[methoxy(polyethylene glycol)-2000] in an 80:20 mol % ratio according to aspects of the present invention.

Thus, according to aspects of the present invention, liposomal formulations of selenium-containing COX-2 inhibitor compositions include at least one polyethylene glycol modified neutral lipid, wherein the total amount of polyethylene glycol modified neutral lipid is an amount in the range of 10-30 molar percent, inclusive, such as 15-25 molar percent polyethylene glycol modified neutral lipid and further including anionic, cationic or neutral lipids, with the proviso that the resulting liposomes have a net neutral surface charge at physiological pH.

According to aspects of the present invention, liposomal formulations of selenium-containing COX-2 inhibitor compositions have an average particle size in the range of 1-100 nm, a neutral or near neutral charge in normal saline and are characterized by stability in normal saline at 4° C. for at least 1-12 months and at 20° C. for at least one month.

Aspects of liposomal formulations of the present invention include a liposomal formulation of selenocoxib-1-GSH with various ratios of ePC:DPPE:PEG-2000. Exemplary ratios of components included in liposomal formulations of the present invention are neutral lipid ePC: DPPE-PEG-2000 in a ratio of 80:20 mol %.

In addition to containing one or more selenium-containing COX-2 inhibitor compositions of the present invention, liposomes of the present invention optionally contain any of a variety of useful biologically active molecules and substances including, but not limited to, one or more additional therapeutic agents, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

A pharmaceutical composition includes a liposomal formulation of selenocoxib-1-GSH in particular aspects of the present invention.

A pharmaceutical composition includes a liposomal formulation of selenocoxib-1-NAC in particular aspects of the present invention.

A pharmaceutical composition includes a liposomal formulation of selenocoxib-1-cysteine in particular aspects of the present invention.

Liposomal formulations of selenium-containing COX-2 inhibitor compositions of the present invention are administered by any appropriate route including, but not limited to, intravenous injection and/or topical application according to aspects of the present invention.

Commercial Packages

Commercial packages are provided according to aspects of the present invention for treating cancer in a subject in need thereof, including a selenium-containing COX-2 inhibitor; selenocoxib-1-GSH, selenocoxib-1-cysteine, selenocoxib-1-N-acetylcysteine; or a pharmaceutically acceptable salt, ester, amide, solvate or stereoisomer thereof. One or more auxiliary components are optionally included in commercial packages of the present invention, such as a pharmaceutically acceptable carrier exemplified by a buffer, diluent or a reconstituting agent.

Aspects of inventive compositions and methods are illustrated in the following examples. These examples are provided for illustrative purposes and are not considered limitations on the scope of inventive compositions and methods.

EXAMPLES

Cell Lines and Culture Conditions

Normal human primary melanocytes containing wild-type B-Raf FOM103 and NHEM 558 are cultured as described in Satyamoorthy K et al., Melanoma Res 1997, 7 Suppl 2:S35-42. Human fibroblast FF2441 cells, metastatic melanoma cell lines harboring mutant $^{V600E}$ B-Raf: UACC 903, A375M (ATCC CRL-1619) and 1205 Lu are maintained in DMEM (Invitrogen), supplemented with 10% FBS (Hyclone). Radial (WM35 harboring mutant $^{V600E}$ B-Raf) and vertical (WM115, WM278.1 both harboring mutant B-Raf) growth phase melanoma cell lines are maintained in Tu2% medium as described in Quong R Y et al., Melanoma Res 1994, 4:313-9. Wild type B-Raf containing C8161.C19 and MelJuSo cell lines were maintained in DMEM supplemented with 10% FBS. Cell lines are maintained in a 37° C. humidified 5% $CO_2$ atmosphere incubator and periodically monitored for genotypic characteristics, tumorigenic potential to confirm cell line identity and phenotypic behavior.

Statistical Analysis

Statistical analysis is performed using Prism 4.0 GraphPad Software. One-way or Two-way Analysis Of Variance (ANOVA) is used for group wise comparisons, followed by the Tukey's or Bonferroni's post hoc tests. For comparison between two groups, the t test is used. Results represent at least two to three independent experiments and are shown as averages S.E.M. Results with a P value less than 0.05 (95% CI) are considered significant.

Western Blot Analysis

Cell lysates are harvested and processed as described in Sharma A et al., Cancer Res 2006, 66:8200-9. Treatment conditions: $1.5 \times 10^6$ melanoma cells are plated in 100 mm culture dishes, 48 h later, treated with celecoxib, selenocoxib-1-GSH (5-20 μmol/L), PLX-4032 (0.2-20 mol/L) or U0126 (2.5-50 μmol/L) for 6 to 72 h. Protein lysates are collected for Western blotting. Blots are probed with total and phospho-Akt (Ser473), phospho-PRAS40 (Thr246), phospho-Erk1/2 (Thr202/Tyr204), total and Phospho-Mek1/2 (Ser217) and cleaved PARP from Cell Signaling Technology (Danvers, Mass.). Total PRAS40 from Invitrogen (Carlsbad, Calif.). Total Erk, cyclin D1, p27, Alpha-enolase and secondary antibodies conjugated with horseradish peroxidase from Santa Cruz Biotechnology (Santa Cruz Biotechnology, Santa Cruz, Calif.). COX-1 and COX-2 antibodies were obtained from Cayman Chemical Company, Ann Arbor, Mich. Immunoblots are developed using the enhanced chemiluminescence detection system (Amersham Pharmacia Biotech, Piscataway, N.J.).

COX-2 expression is elevated in advanced melanoma patient tumors and melanoma cell lines.

The expression of COX-2 is measured by Western blotting in a panel of melanoma patient tumors and cell lines representing radial (WM35), vertical (WM115, WM278.1) and metastatic (A375M, UACC 903, 1205 Lu) stages of development. For analysis of human melanoma tumors, tissue samples are collected from 25 patients at surgery, immediately snap frozen in liquid nitrogen, and stored at −80° C. until protein lysate collection. Tumors are pulverized using a mortar and pestle chilled in liquid nitrogen to collect protein for Western blotting. Protein lysates are extracted from tumors as described in Madhunapantula S V et al., Cancer Res 2007, 67:3626-36, and analyzed by Western blotting to measure levels of COX-2. COX-2 protein levels in tumors are normalized to an Alpha-enolase loading control and relative COX-2 expression quantified using ImageJ software.

FIG. 1A shows elevated levels of COX-2 expression in melanoma patient tumors and cell lines. Results are normalized to Alpha-enolase loading and compared to normal human melanocyte controls. 76% (19/25) of melanoma patient tumors had elevated COX-2 expression when compared to normal human melanocyte control (NHEM) cells.

Figure 1B:
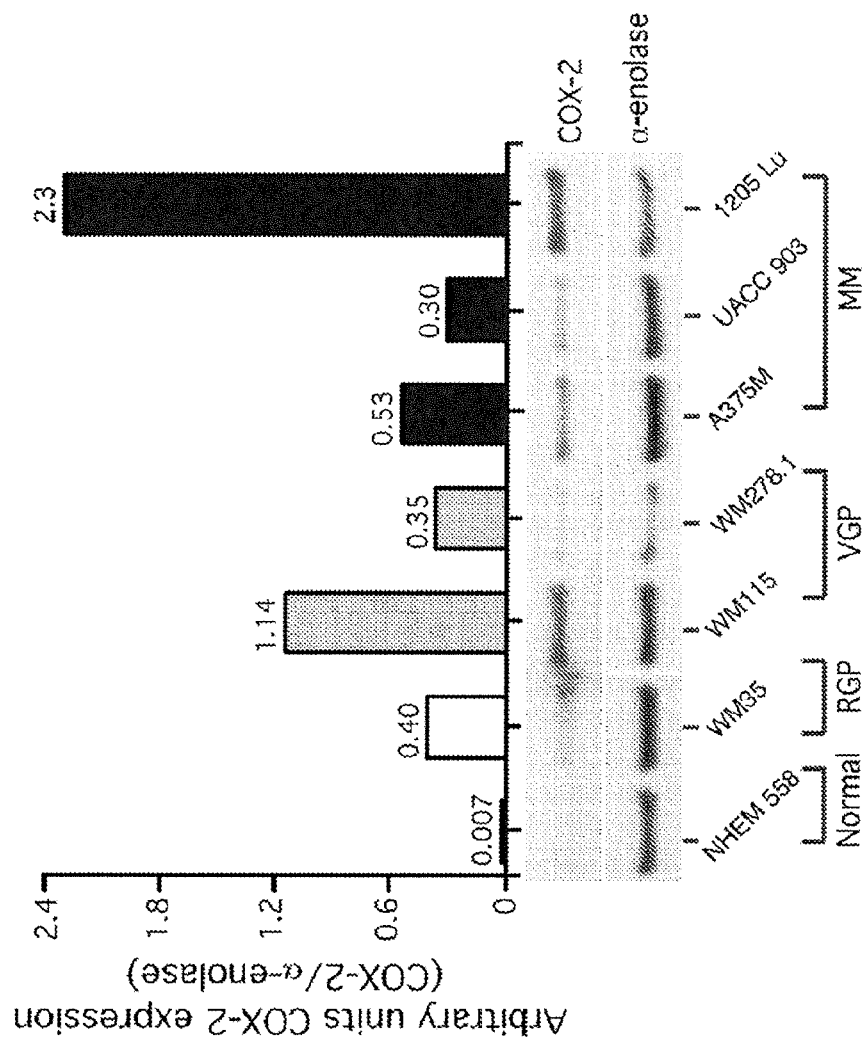
FIG. 1B is a graph and image of a Western blot showing that COX-2 expression is increased in a cell line based melanoma tumor progression model.

All melanoma cell lines examined expressed levels of COX-2 protein higher than that observed in melanocytes, albeit, in varying amounts. FIG. 1B shows that COX-2 expression is increased in a cell line based melanoma tumor progression model. Lysates collected from normal human melanocytes, radial (WM3S), vertical (WM115, WM278.1), and metastatic (A375M, UACC and 1205 Lu) stage cell lines are subjected to Western blot analysis and probed for COX-2. Alpha-enolase serves as a control for equal protein loading. Expression of COX-2 in UACC 903, A375M and 1205 Lu cell lines is 43, 76 and 329-fold higher respectively, than that observed in melanocytes.

SiRNA Efficacy and Knockdown Studies:

To determine efficacy of siRNA-mediated knockdown, 200 pmoles of siCOX-2 #1 or siCOX-2 #2, is compared to scrambled siRNA or reconstitution buffer following nucleofection into $1 \times 10^6$ of 1205 Lu and A375M cells using an Amaxa nucleofector with solution R/program K-17 (1205 Lu) or A-23 (A375M). Transfection efficiency of viable cells is 70-80%. Following siRNA transfection, cells recovered for 2 days and are replated in 96-well plates to measure cell viability using the MTS assay (CellTiter 96 AQueous Cell Proliferation Assay, Promega, Madison, Wis.). To show siRNA-mediated protein knockdown in vitro, $1 \times 10^6$ of 1205 Lu, UACC 903 (Program K-17) and A375M cells are similarly nucleofected with 200 pmoles of siCOX-2 #1, siCOX-2 #2, and 100 pmoles of $^{V600E}$B-RAF, MEK1, MEK2, ERK1, and ERK2, scrambled siRNA, reconstitution buffer, and protein lysates are harvested at day 4 or 6, and analyzed by Western blot analysis. Duplexed Stealth siRNA (Invitrogen, Carlsbad, Calif.) is used for these studies. The following siRNA sequences are used: COX-2 #1: UCC AGA CAA GCA GGC UAA UAC UGA U (SEQ ID NO: 1); COX-2 #2: GAG UUA UGU CUU GAC AUC CAG AUC A (SEQ ID NO: 2). SiRNA sequences for scrambled, $^{V600E}$, B-RAF, MEK1, MEK2, ERK1, and ERK2 as described in Sharma A et al., Cancer Res, 2006, 66:8200-9.

Figure 1C:
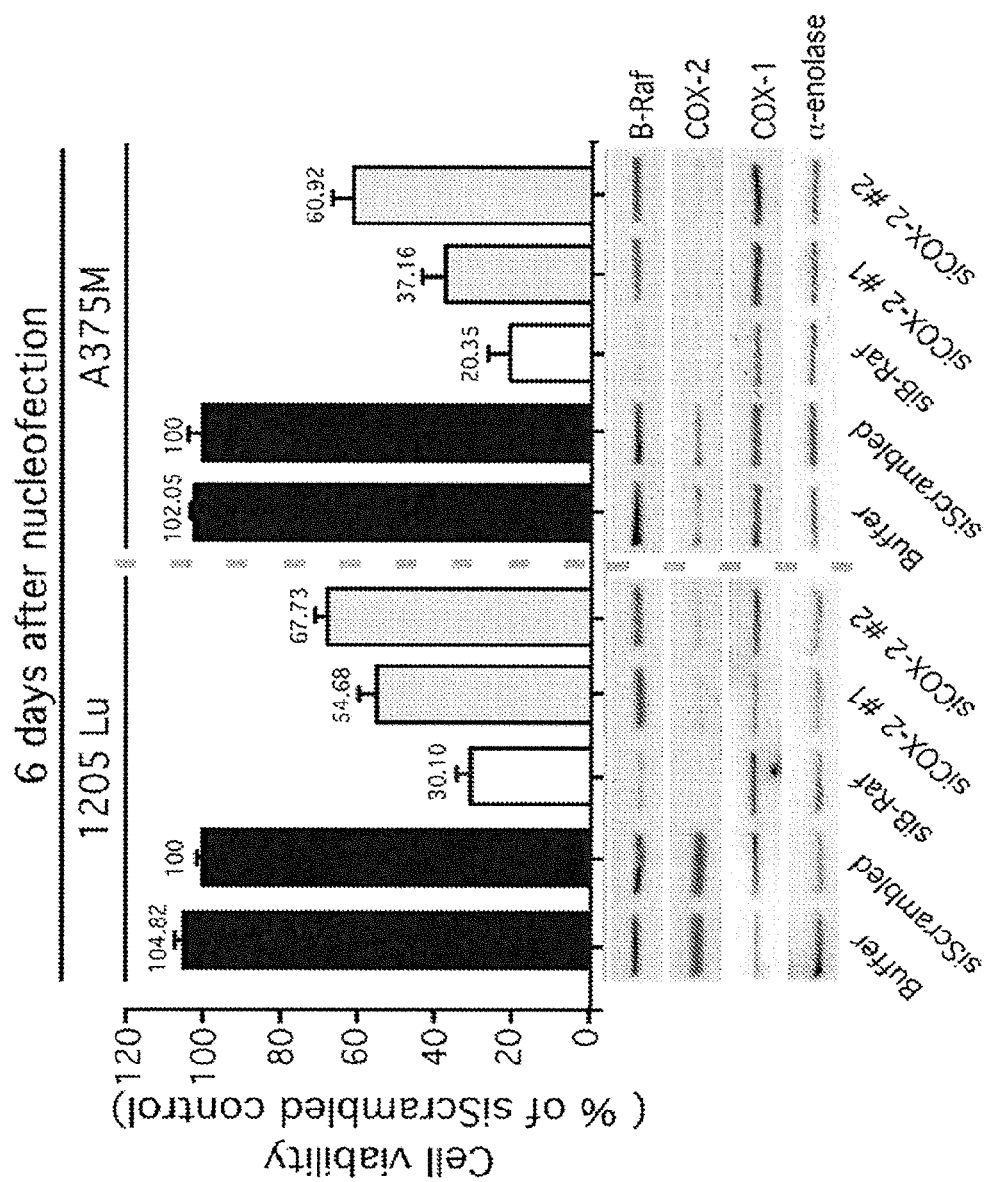
FIG. 1C is a graph and image of a Western blot showing that targeting COX-2 using siRNAs decreased melanoma cell viability.

Reduction of COX-2 protein levels using siRNA targeting $^{V600E}$ B-Raf or COX-2 decreased melanoma cell viability. To determine whether targeting COX-2 would reduce viability of melanomas, metastatic 1205 Lu and A375M cells that express relatively high levels of protein are transfected with 2 different siRNAs targeting different regions of the mRNA and cell viability compared to controls nucleofected with a scrambled siRNA or buffer. FIG. 1C shows that targeting COX-2 using siRNAs decreased melanoma cell viability. 1205 Lu and A375M melanoma cells are nucleofected with two non-overlapping siRNAs against COX #1 and #2 using solution R/program K-17 (1205 Lu) or solution R/program A-23 (A375M). Targeting COX-2 reduced melanoma viability by 32 to 63%. siRNA targeting mutant $^{V600E}$B-Raf serves as a positive control. Alpha-enolase serves as a control for equal protein loading.

In both cell lines, targeting COX-2 reduced melanoma viability by 32 to 63%. Targeting mutant $^{V600E}$B-Raf using siRNA reduced COX-2 expression, suggesting that protein expression is regulated through this pathway, FIG. 1C. Levels of COX-2 protein decreased when $^{V600E}$B-Raf expression levels are targeted using siRNA.

Figure 1D:
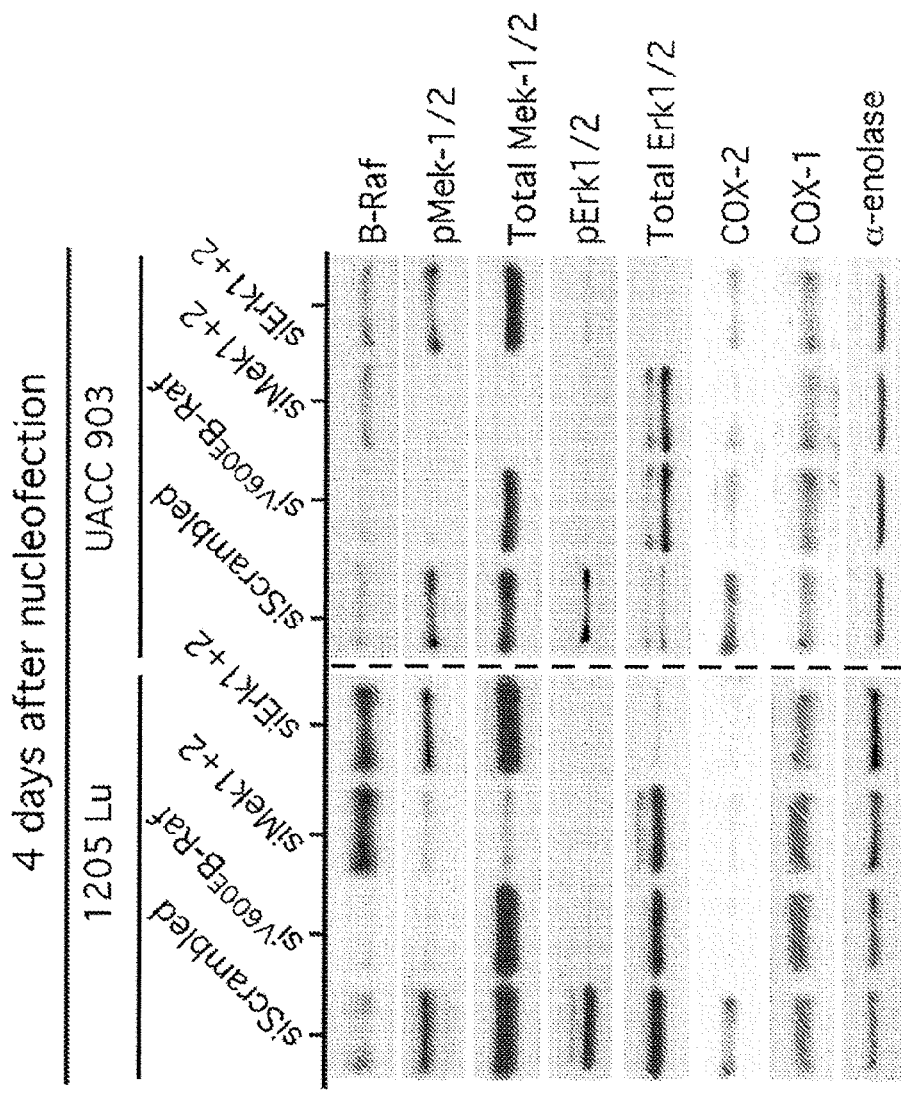
FIG. 1D is an image of a Western blot showing that SiRNA mediated inhibition of the MAP kinase pathway decreased COX-2 expression in melanomas.

SiRNA and pharmacological agents targeting the $^{V600E}$B-Raf confirm that COX-2 expression is regulated through $^{V600E}$B-Raf signaling pathway in melanomas. To examine whether siRNA-mediated targeting of Mek1/2 and Erk1/2, downstream of $^{V600E}$B-Raf, would decrease COX-2 expression, siRNA or pharmacological agents are used to down regulate protein expression or activity. 1205 Lu and UACC 903 cells are nucleofected with siRNAs inhibiting mutant $^{V600E}$B-Raf, downstream Mek1/2 or Erk1/2. A significant decrease in COX-2, but not the COX-1 isoform, is observed when each of the members of the $^{V600E}$B-Raf, signaling pathway is targeted. FIG. 1D shows that SiRNA mediated inhibition of the MAP kinase pathway decreased COX-2 expression in melanomas. 1205 Lu and UACC 903 cells are nucleofected with siRNAs inhibiting mutant $^{V600E}$B-Raf, Mek1 or Mek2 and Erk1 or Erk2. Compared to cells treated with scrambled siRNA, decreasing protein levels of each member of the MAP kinase pathway led to a decrease in COX-2 but not COX-1 levels. Alpha-enolase serves as a control for equal protein loading.

Figure 1E:
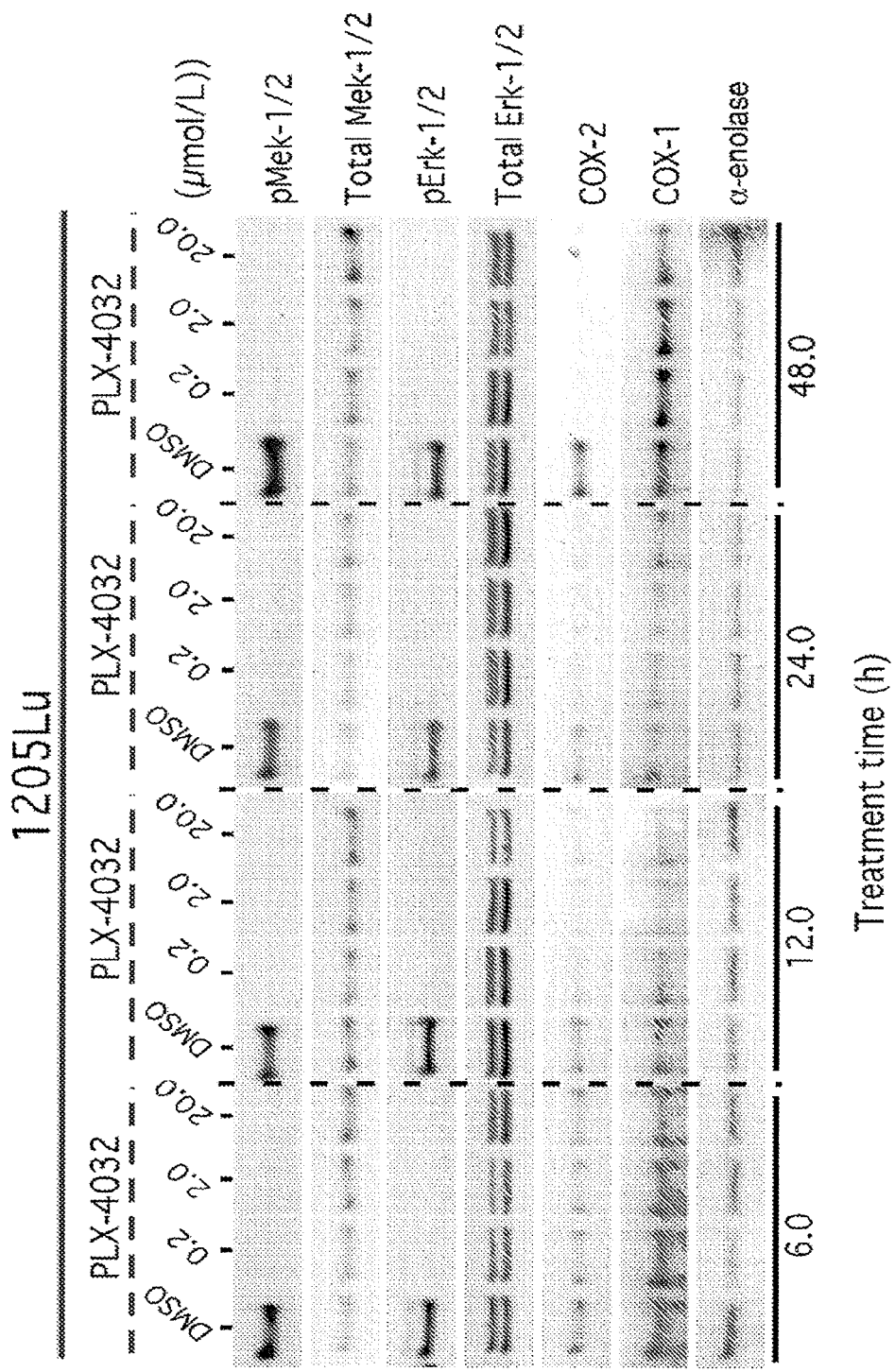
FIG. 1E is an image of a Western blot showing that that PLX-4032 targeting of $^{V600E}$B-Raf decreased COX-2 expression in 1205 Lu melanoma cells.
Figure 1F:
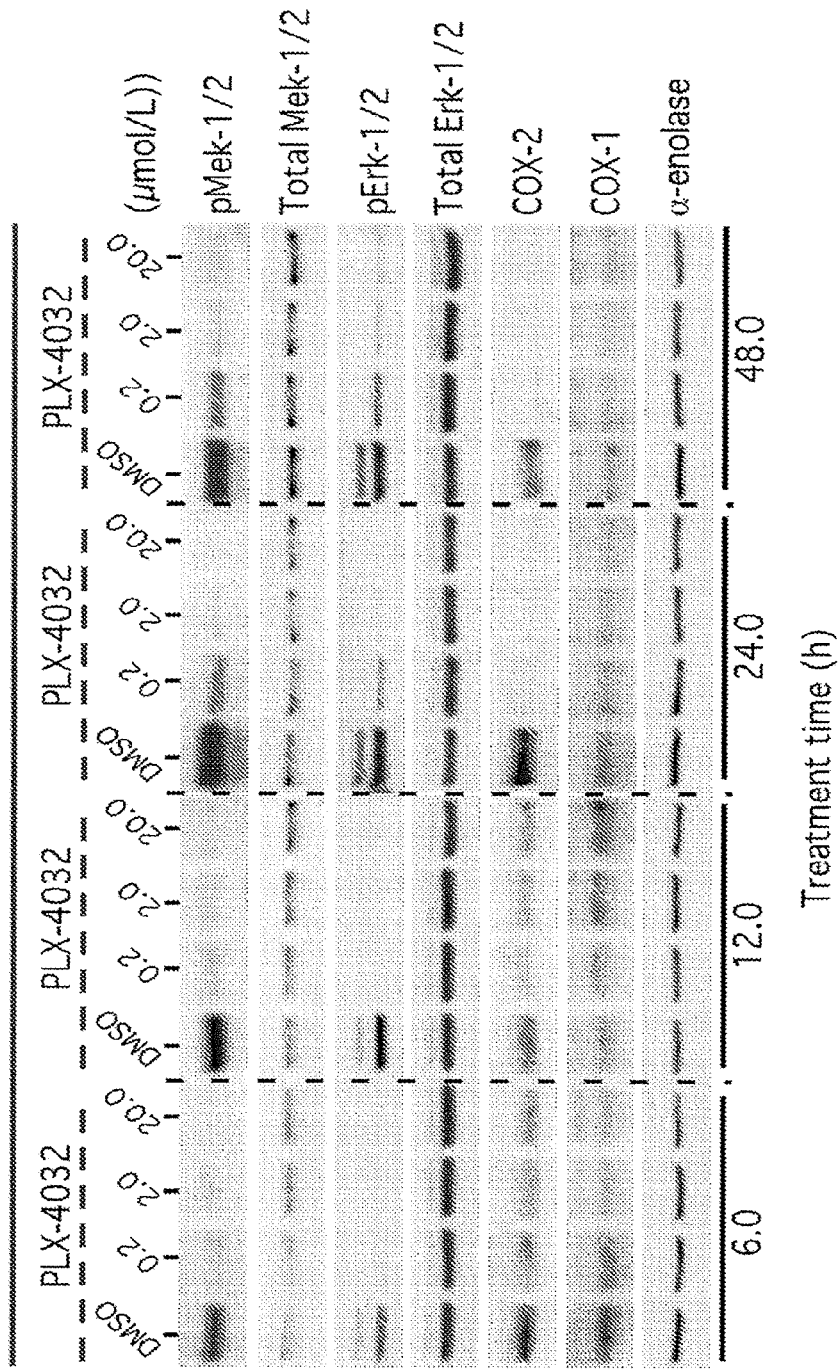
FIG. 1F is an image of a Western blot showing that that PLX-4032 targeting of $^{V600E}$B-Raf decreased COX-2 expression in UACC 903 melanoma cells.

Vemurafenib (PLX-4032), a $^{V600E}$B-Raf inhibitor, is used to inhibit activity of this pathway. Cells treated with PLX-4032 showed decreased COX-2 protein expression beginning after 12 h of treatment. The changes are more evident following 12, 24 and 48 h of treatment in the case of 1205 Lu, FIG. 1E. In the case of UACC 903 cells, a significant decrease is seen after 24 and 48 h of treatment, FIG. 1F. Similar to siRNA studies, no changes are observed in COX-1 expression in either cell line under these treatment conditions, FIGS. 1C and 1D. A decrease in phosphorylation, but not expression of Mek1/2 and Erk1/2 proteins showed the inhibitory activity of PLX-4032 on the $^{V600E}$B-Raf pathway. FIGS. 1E-F show that PLX-4032 targeting of $^{V600E}$B-Raf decreased COX-2 expression. 1205 Lu or UACC 903 cells are treated with 0.2-20 μmol/L PLX-4032 for 6, 12, 24 and 48 h. Levels of pMek1/2, pErk1/2, and COX-2 decreased following after 12 h of drug treatment. No changes are seen in COX-1 expression. Alpha-enolase serves as a control for equal protein loading.

Figure 1G:
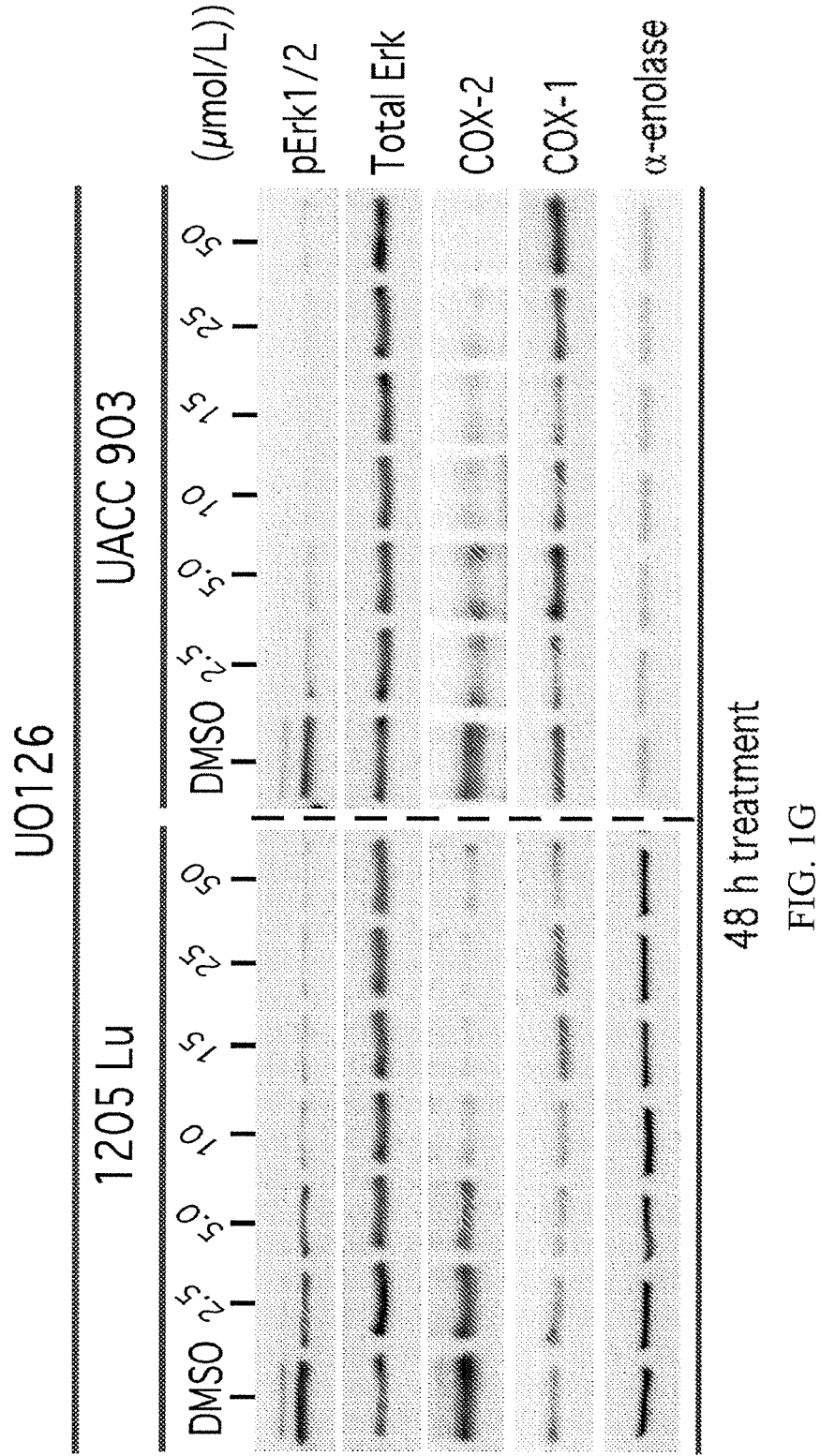
FIG. 1G is an image of a Western blot showing that U0126 targeting of Mek1/2 decreased COX-2 expression in 1205 Lu and UACC 903 melanoma cells.

Like PLX-4032, Mek1/2 inhibitor U0126 also reduces the expression of COX-2 without affecting COX-1 in 1205 Lu and UACC 903 cell lines. FIG. 1G shows that U0126 targeting of Mek1/2 decreased COX-2 expression. 1205 Lu or UACC 903 cells are treated with 2.5-50 μmol/L U0126 for 48 h. Levels of pErk1/2 and COX-2 similarly decrease following drug treatment with no changes in COX-1 expression. Alpha-enolase serves as a control for equal protein loading.

Targeting $^{V600E}$B-Raf or downstream proteins in the signaling cascade reduces expression of COX-2 in melanomas and decreases the proliferative potential of the cells. Thus, COX-2 lies downstream of $^{V600E}$B-Raf, Mek-1/2 and Erk-1/2 in this signaling pathway.

Synthesis of celecoxib, selenocoxib-1 and selenocoxib-1-GSH

Celecoxib is synthesized as described in detail in Penning T D et al. J Med Chem 1997; 40: 1347-65. Selenocoxib-1 is prepared as described in Desai D et al., Chem Biol Interact 2010; 188: 446-56.

Selenocoxib-1-GSH is prepared by reacting molar equivalent selenocoxib-1 with glutathione in tetrahydrofuran: $H_2O$ (2:1) mixture. pH is adjusted to slightly basic to give selenocoxib-1-GSH conjugate in quantitative yield as yellow powder. MP:196-198° C.; $^1$H NMR (DMSO-$d_6$, 500 MHz) δ 1.72-1.83 (m, 3H), 1.88-1.98 (m, 1H), 2.23-2.36 (m, 2H), 2.91 and 2.94 (dd, 1H, J=10 Hz), 3.16 and 3.18 (dd, 1H, J=4.5 Hz), 3.57-3.72 (m, 3H), 4.18 and 4.23 (dd, 2H, J=12.5 Hz and 22 Hz), 4.51 (td, 1H, J=4.0 Hz), 6.62 (s, 1H, CH), 7.25 (d, 1H, aromatic, J=2.5 Hz), 7.26 (d, 1H, aromatic, J=3.5 Hz), 7.35-7.39 (m, 3H, aromatic), 7.41 (dt, 2H, aromatic, J=8.5 Hz and 2.0 Hz), 7.79 (dt, 2H, aromatic, J=8.5 Hz and 2.0 Hz), 8.44 (d, 1H, J=7 Hz), 8.75 (ds, 1H); MS (M/Z, Intensity): 681 (M+, 100). The identities of the compounds are confirmed by nuclear magnetic resonance as well as mass spectra analysis, and purity (>99%) is quantified by high-performance liquid chromatography analysis.

Selenocoxib-1-NAC Preparation

To a solution of selenocoxib-1 (2.0 mmol) in THF (25 mL) at 0° C. is added a solution of N-acetylcysteine (326 mg, 2.0 mmol) in water (15 mL), and to this mixture 2% NaOH (0.1 mL) is added. The reaction mixture is allowed to warm to room temperature and stirred for 12 h. The mixture is washed with hexane (2×5 mL), and the aqueous layer is acidified with 2 N HCl and extracted with ethyl acetate. The organic layer is separated, dried (MgSO4), and concentrated in vacuum to give selenocoxib-1-NAC in quantitative yield.

Selenocoxib-1-Cysteine Preparation

To a solution of selenocoxib-1 (2.0 mmol) in THF (25 mL) at 0° C. is added a solution of cysteine (326 mg, 2.0 mmol) in water (15 mL), and to this mixture 2% NaOH (0.1 mL) is added. The reaction mixture is allowed to warm to room temperature and stirred for 12 h. The mixture is washed with hexane (2×5 mL), and the aqueous layer is acidified with 2 N HCl and extracted with ethyl acetate. The organic layer is separated, dried (MgSO4), and concentrated in vacuum to give selenocoxib-1-cysteine in quantitative yield.

Figure 2A:
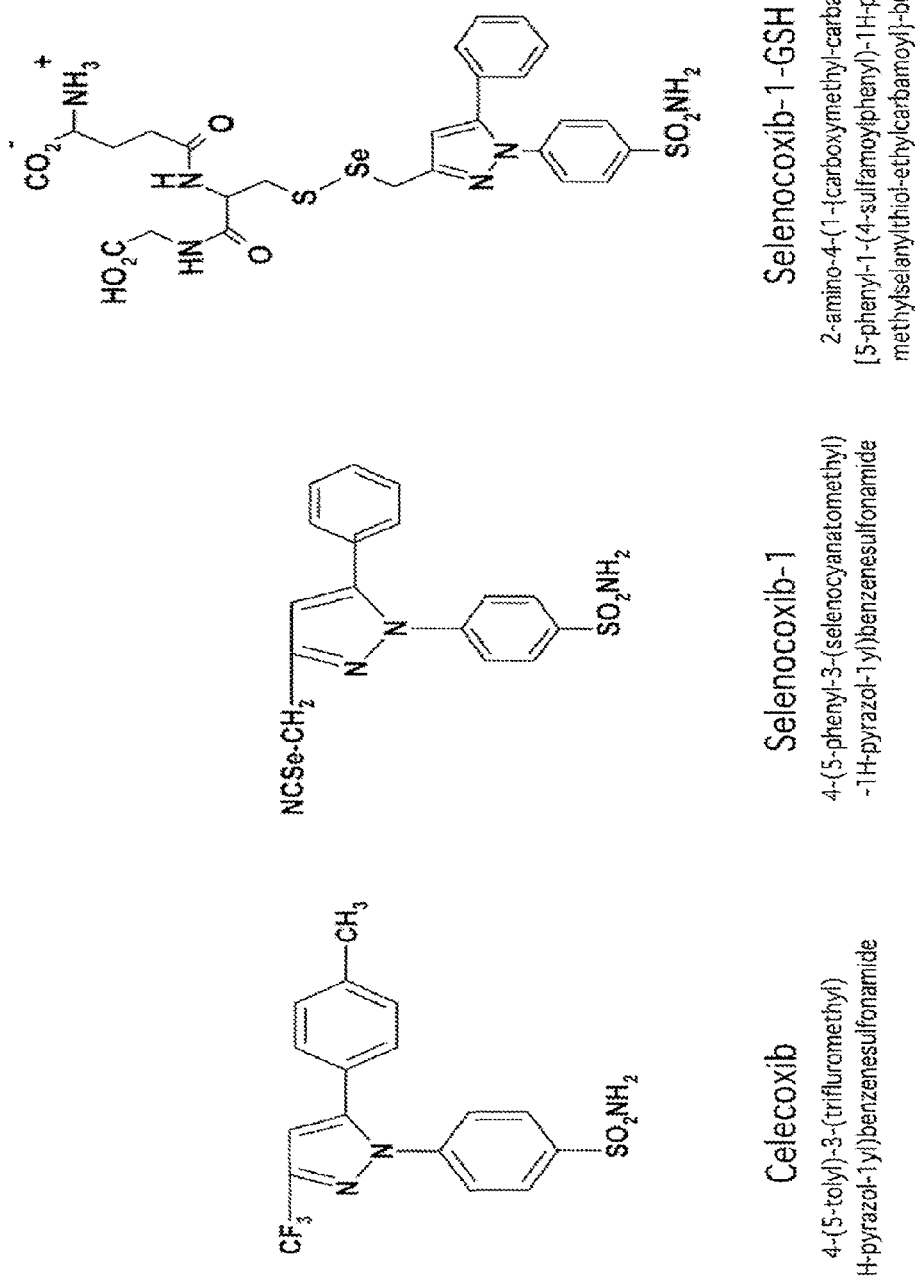
FIG. 2A shows chemical structures of celecoxib, selenocoxib-2 and selenocoxib-1-GSH.
Figure 2B:
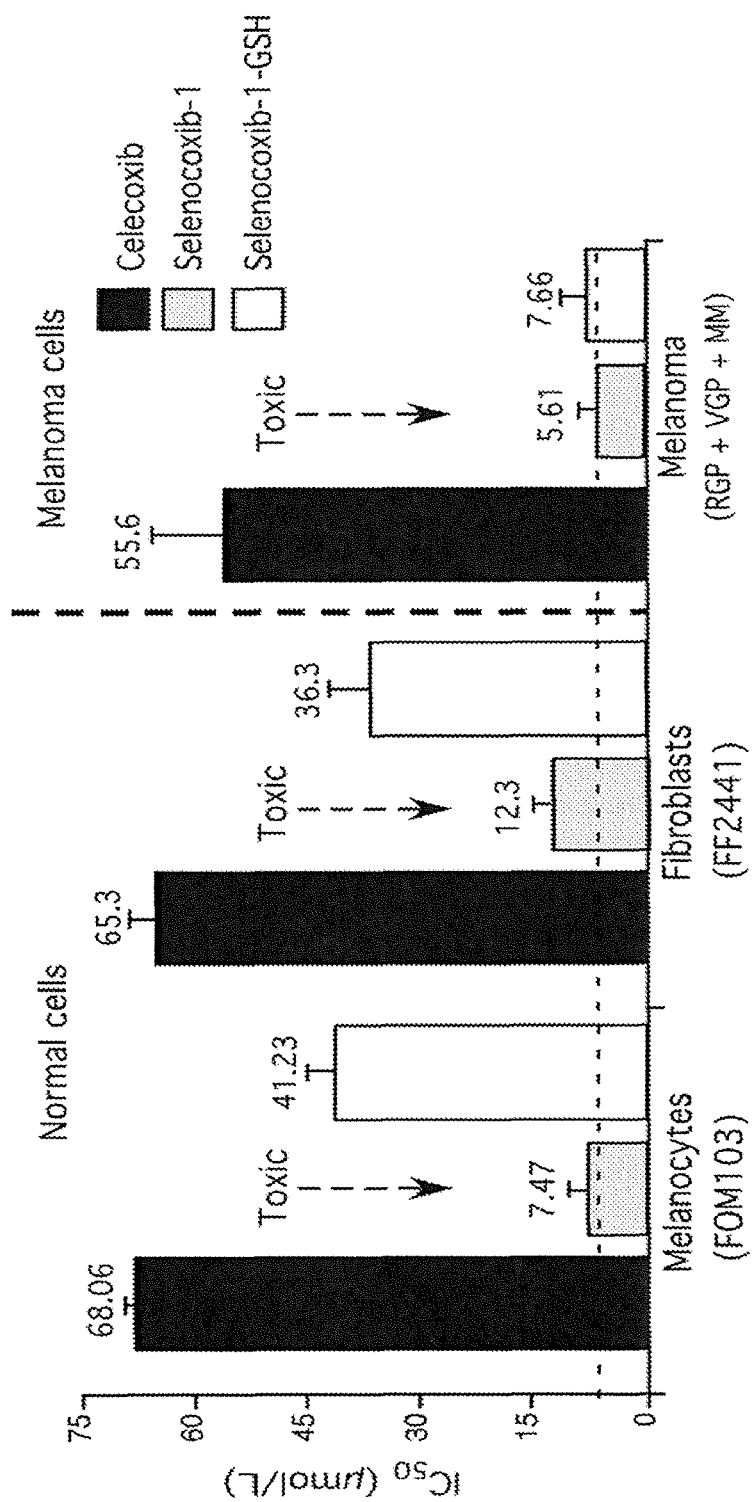
FIG. 2B is a graph showing that the number of inhibited normal cells is significantly reduced compared to the number of inhibited cancer cells when both are treated with selenocoxib-1-GSH.

Unexpectedly, selenocoxib-1-GSH has significantly lower toxicity on normal cells and has melanoma cell killing efficacy, FIG. 2B. Selenocoxib-1 inhibited melanoma cell viability and also reduces normal cell growth with $IC_{50}$s similar to that of melanoma cells, indicating toxicity. Surprisingly, selenocoxib-1-GSH has an increased differential inhibition ratio, that is, the number of inhibited normal cells is significantly reduced compared to the number of inhibited cancer cells when both are treated with selenocoxib-1-GSH, FIG. 2B. Selenocoxib-1-GSH, but not selenocoxib-1, inhibits the growth of melanoma cells with a lesser effect on the growth of normal human melanocytes or fibroblast cells. Similar results are expected with selenocoxib-1-cysteine and selenocoxib-N-acetylcysteine.

Toxicity of selenocoxib-1 but not selenocoxib-1-GSH is observed in animal studies. Animal survival and body weight loss following treatment with celecoxib, selenocoxib-1 or selenocoxib-1-GSH. Celecoxib (0.127 μmoles), selenocoxib-1 (0.032-0.064 μmoles) or selenocoxib-1-GSH (0.127-0.254 μmoles) are injected intraperitoneally daily for seven days (3 mice/group). Number of mice surviving and changes in body weight after 7 days of drug treatment is scored (Table I).

Celecoxib at 0.127 μmoles led to death of all animals following 7 days of treatment, while selenocoxib-1 at concentrations of 0.032-0.064 moles, (equivalent to ppm selenium) leads to weight losses of 14% or 100% animal mortality after seven days of treatment (Table I). In contrast, animals receiving 0.127 to 0.254 moles (equivalent to 5 to 10 ppm of selenium) of selenocoxib-1-GSH exhibit negligible weight loss of ~2% and no mortality is observed. These data are summarized in Table I.

TABLE I

| Compounds | Doses (μmoles, equivalent to ppm selenium) | Doses (PPM) | Mortality at Day 7 | % of weight loss |
|---|---|---|---|---|
| Celecoxib | 0.127 | — | 3/3 | — |
| Selenocoxib-1 | 0.032 | 2.5 | 0/3 | 14.07 |
|  | 0.064 | 5.0 | 3/3 | — |
| Selenocoxib-1-GSH | 0.127 | 10 | 0/3 | No loss |
|  | 0.254 | 20 | 0/3 | 2.0 |

Cyclooxygenase Inhibition

Human recombinant COX-2 activity is assayed using a commercial COX-inhibitor screening assay kit (Cayman Chemical, Ann Arbor, Mich.) and following the manufacturer's protocol. The concentrations of celecoxib and selenocoxib-1-GSH tested are 0.2, 2.0 and 20 nM. SC-560 and DuP-697, standard inhibitors for COX-1 and COX-2 respectively, are tested as positive controls. DMSO serves as the negative controls (100% activity). The product of this enzymatic reaction is determined spectrophotometrically at 405 nm. The optical activity is proportional to the amount of PG-acetylcholinesterase conjugate bound to the well, which is inversely proportional to the amount of PGs present in the well during incubation. This assay is performed in duplicate.

Figure 2C:
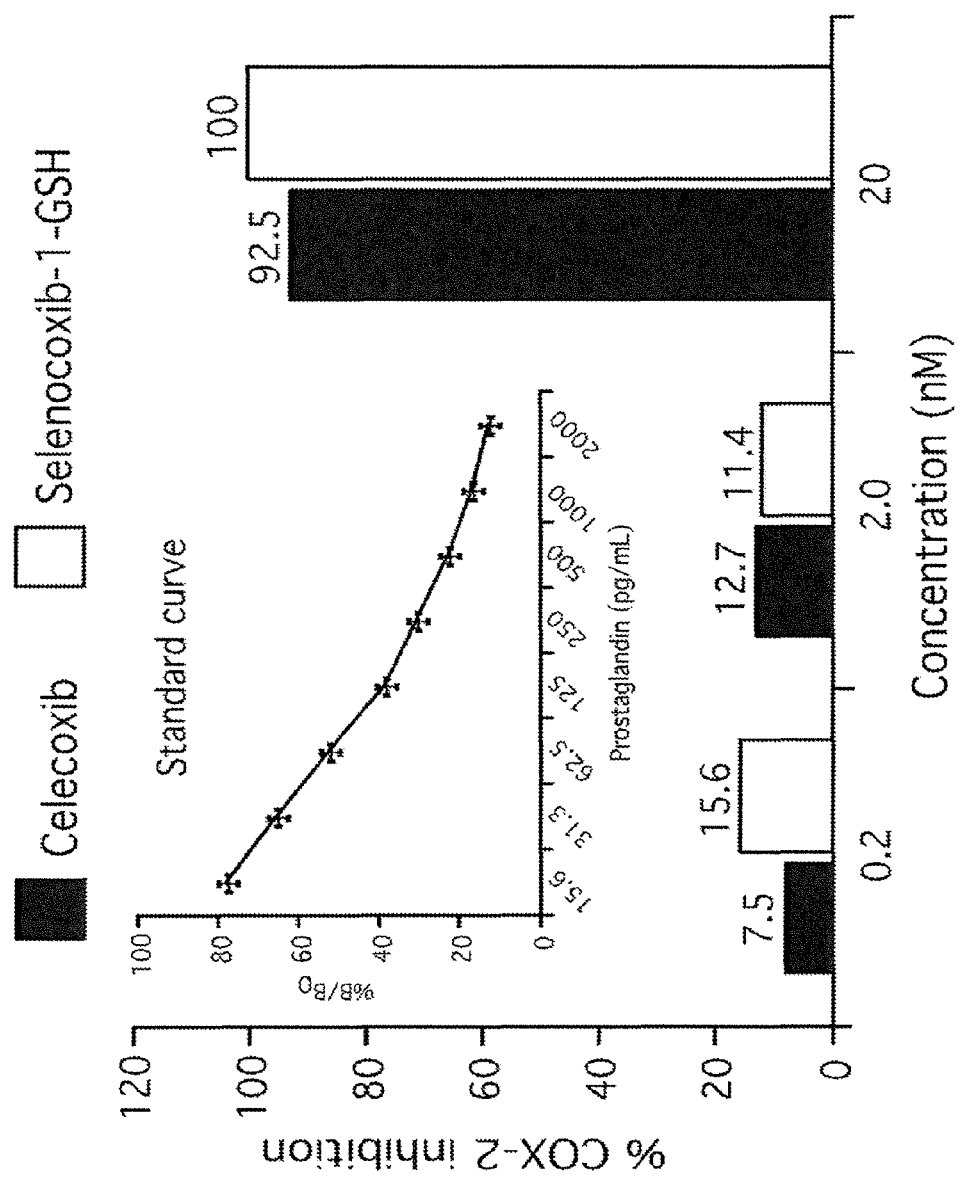
FIG. 2C is a graph showing that selenocoxib-1-GSH has COX-2 inhibitory activity.

FIG. 2C shows that selenocoxib-1-GSH has COX-2 inhibitory activity. Human recombinant COX-2 activity is assayed using a commercial COX-inhibitor screening assay kit. 0.2, 2.0 and 20 nM of celecoxib and selenocoxib-1-GSH of are tested and shown to retain COX-2 inhibitory activity. DMSO serves as the negative controls (100% activity). The product of this enzymatic reaction is determined spectrophotometrically at 405 nm. Assay is performed in 2 independent experiments.

Cell viability, proliferation, apoptosis and cell cycle analysis: Viability and $IC_{50}$ (µmol/L) of normal human melanocytes, fibroblast and melanoma cells following treatment with inhibitors are measured using the MTS assay (Promega, Madison, Wis.) described in Sharma A, et al., Clin Cancer Res 2009; 15:1674-85; and Madhunapantula S V, et al., Mol Cancer Ther 2008; 7:1297-308. In brief, $5 \times 10^3$ cells per well in 100 µL of media are plated and grown in a 96-well plate for 36 to 72 h respectively for melanoma (WM35, WM115, 1205 Lu and UACC 903) and normal cell lines (FOM103 and FF2441) treated 0.312 to 100 µmol/L of celecoxib, selenocoxib-1 and selenocoxib-1-GSH for 24, 48 or 72 h with DMSO as vehicle control. $IC_{50}$ values for each inhibitor in µmol/L for respective cell lines are measured from three independent experiments using GraphPad Prism version 4.01 (GraphPad Software, La Jolla, Calif.).

Figure 3A:
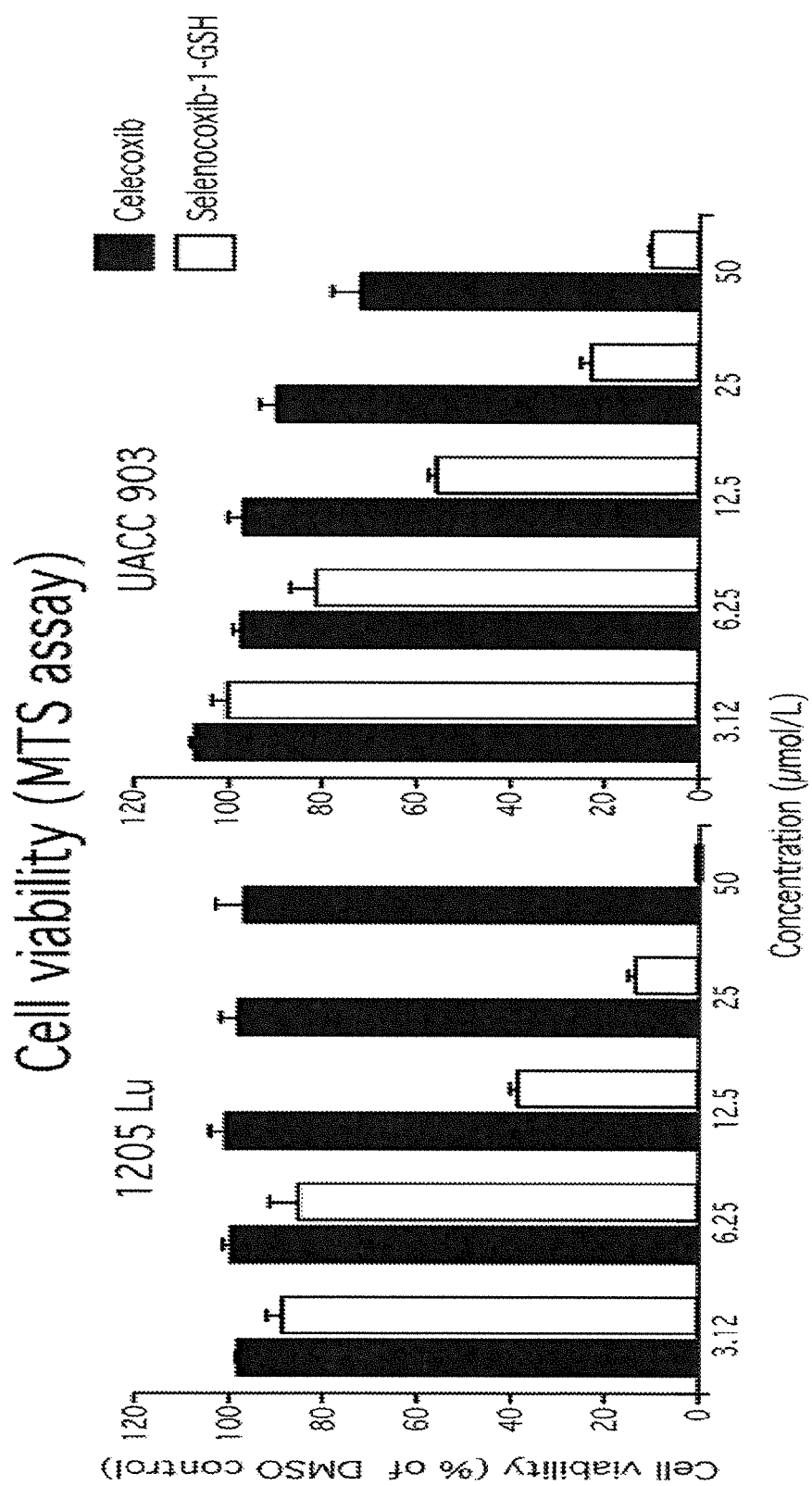
FIG. 3A is a graph showing that selenocoxib-1-GSH but not celecoxib inhibits 1205 Lu and UACC 903 melanoma cell viability.
Figure 3B:
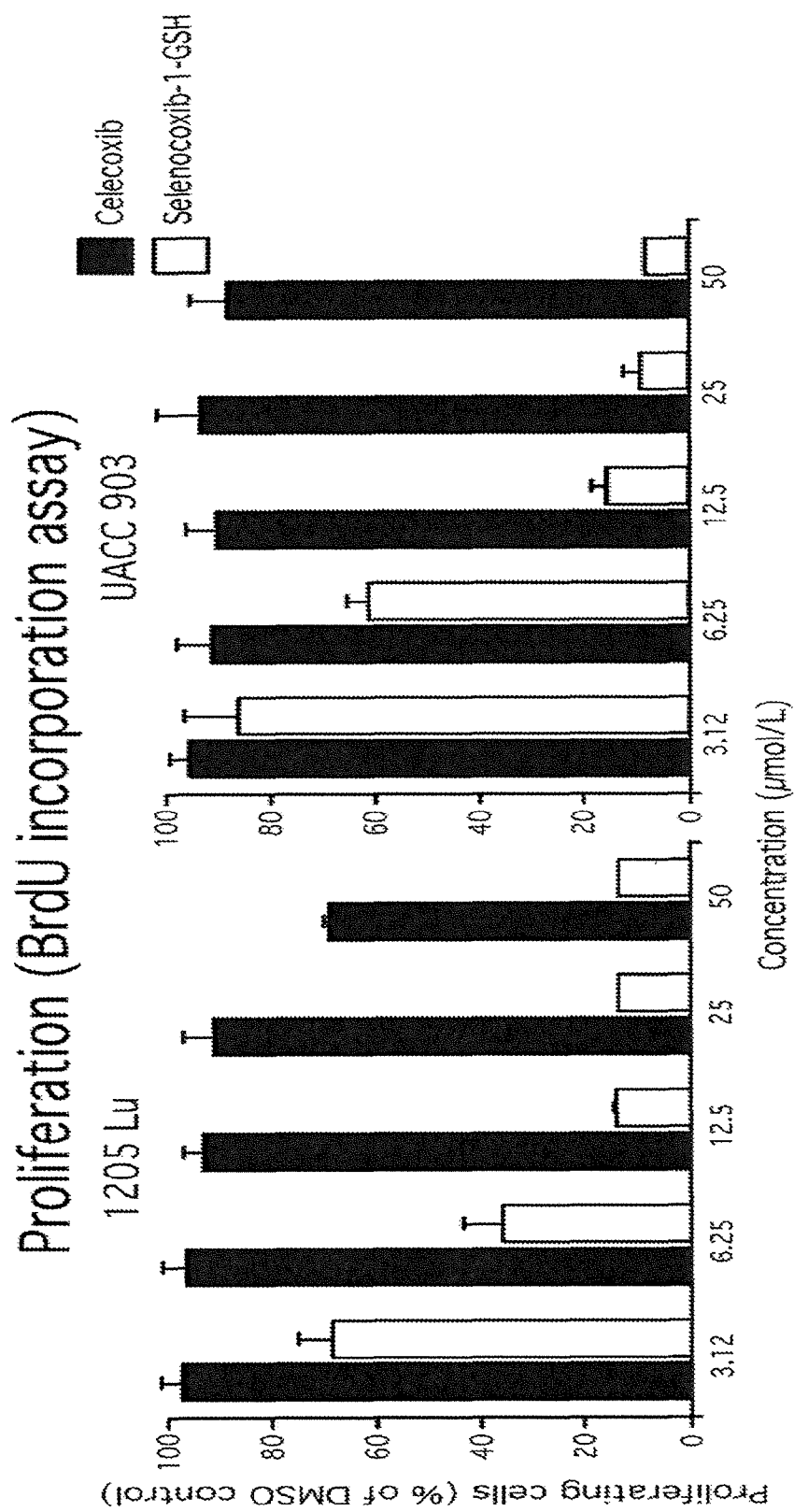
FIG. 3B is a graph showing that selenocoxib-1-GSH reduces proliferation of 1205 Lu and UACC 903 melanoma cells.
Figure 3C:
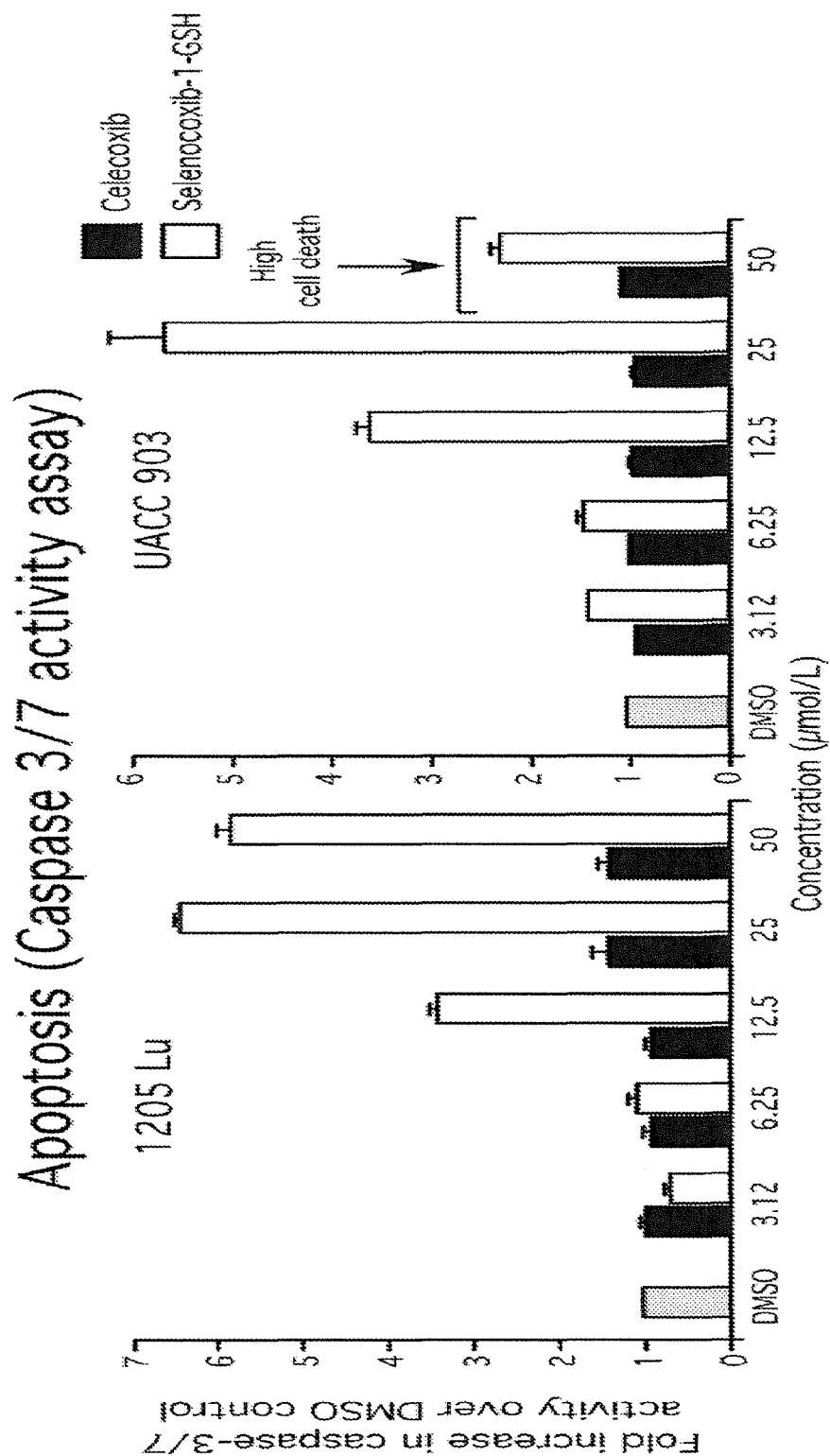
FIG. 3C is a graph showing that selenocoxib-1-GSH increases caspase-3/7 activity, which is an indicator of apoptosis, in 1205 Lu and UACC 903 melanoma cells.

FIGS. 3A, 3B & 3C show that selenocoxib-1-GSH, but not celecoxib, inhibited melanoma cell proliferation and induced apoptosis. 1205 Lu and UACC 903 cells are treated with increasing concentrations of celecoxib and selenocoxib-1-GSH for 72 h and cell viability, proliferation and apoptosis rates measured by MTS, BrdU incorporation and caspase-3/7 assays, respectively. Data represent averages of at least 3 independent experiments; bars; S.E.M.

Dose response curves generated using 1205 Lu and UACC 903 cell lines demonstrate that selenocoxib-1-GSH but not celecoxib inhibits melanoma cell viability, FIG. 3A. At 12.5 µmol/L, selenocoxib-1-GSH leads to a 40 to 60% decrease in cell viability compared to control DMSO vehicle treated cells, FIG. 3A. Furthermore, selenocoxib-1-GSH inhibited the growth of melanoma cell lines irrespective of B-Raf mutation status.

Table II shows that selenocoxib-1-GSH kills melanoma cells more effectively than normal cells. Normal and melanoma cells are seeded in to a 96-well plate and after 36 to 72 h, treated with increasing concentrations of celecoxib, selenocoxib-1 or selenocoxib-1-GSH for the indicated time period. The number of viable cells is measured using MTS and percentage decrease in viability calculated. $IC_{50}$ values for each inhibitor in µmol/L for respective cell lines are measured from three independent experiments using GraphPad Prism version 4.01 (GraphPad Software, La Jolla, Calif.).

Applied Sciences, Indianapolis, Ind.) and Apo-ONE Homogenous caspase-3/7 assay kit (Promega, Madison Wis.), as described in Sharma A, et al., Clin Cancer Res 2009; 15:1674-85; and Madhunapantula S V, et al., Mal Cancer Ther 2008; 7:1297-308.

Selenocoxib-1-GSH reduces proliferation of 1205 Lu and UACC 903 melanoma cells, FIG. 3B, and increases caspase-3/7 activity, which is an indicator of apoptosis, in a dose dependent manner up to 25 µmol/L, FIG. 3C. A significant decrease in caspase-3/7 activity is observed when UACC 903 cells are treated with 50 µmol/L selenocoxib-1-GSH, which can be attributed to massive cell death caused by degradation of cellular proteins, FIG. 3C.

Figure 3D:
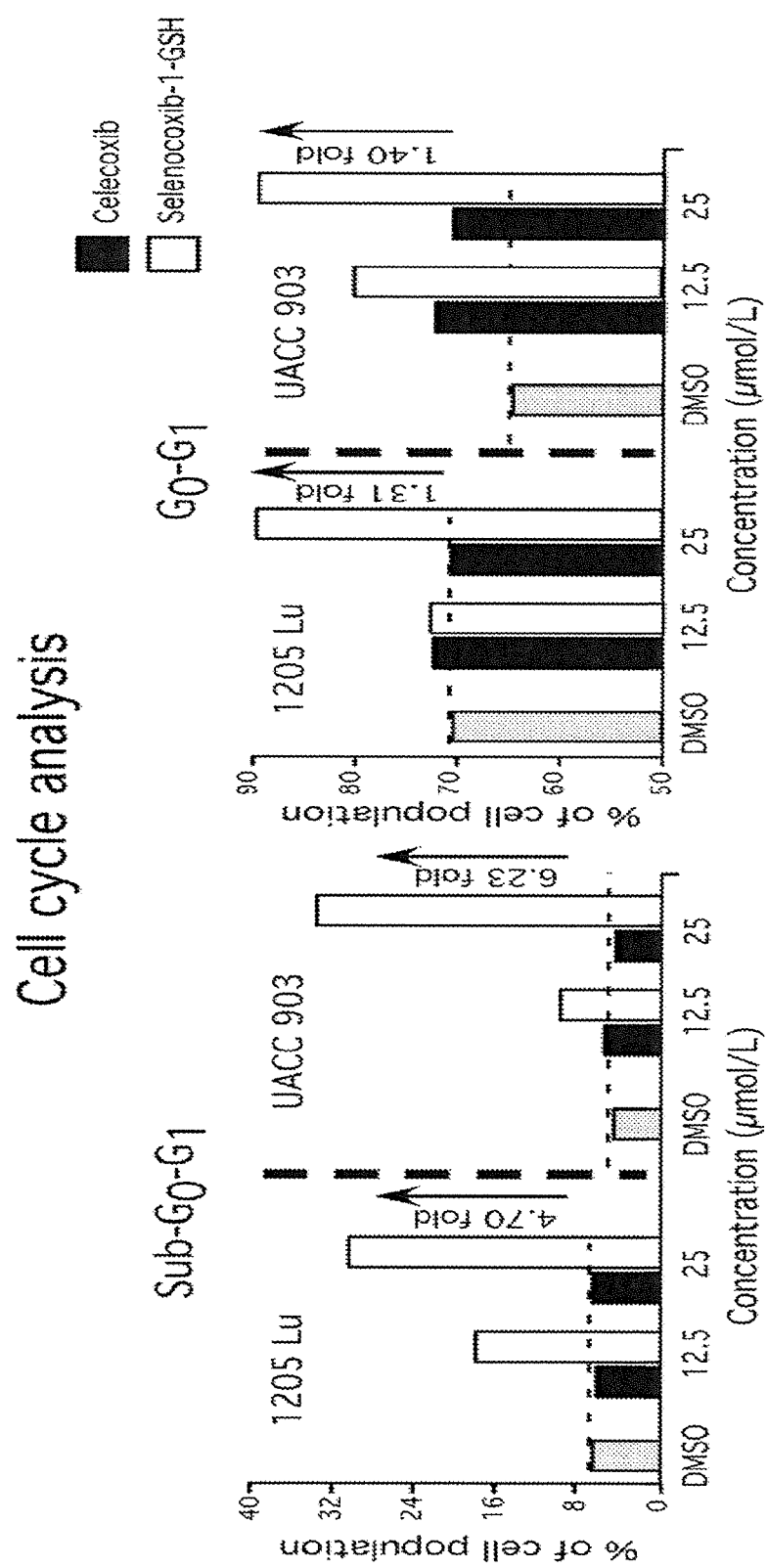
FIG. 3D is a graph showing that selenocoxib-1-GSH arrests melanoma cells in the $G_0$-$G_1$ phase of the cell cycle.

The effect of selenocoxib-1-GSH on cell cycle distribution is measured by analyzing propidium iodide stained 1205 Lu and UACC 903 cells using a BD FACScan. Melanoma cells 1205 Lu and UACC 903 are grown in 100-mm culture dishes followed by treatment with 12.5 and 25 µmol/L of celecoxib and selenocoxib-1-GSH for 72 h (FIG. 3D). Total floating and adherent cells are collected following trypsinization and stained using a 1 mL propidium iodide solution containing 100 µg/mL propidium iodide; (Sigma, St Louis, Mo.), 20 µg/mL Ribonuclease A (Roche diagnostics, Indianapolis, Ind.) and 3 µg/mL Triton X-100 dissolved in 0.1% (W/V) sodium citrate for 30 m at 4° C. Stained cells are analyzed using the FACScan analyzer (Becton Dickinson, Franklin lakes, NJ) and data processed utilizing ModFit LT software (Verity Software House, Topsham, Me.) as described in Sharma A, et al., Clin Cancer Res 2009; 15:1674-85; and Madhunapantula S V, et al., Mol Cancer Ther 2008; 7:1297-308.

Selenocoxib-1-GSH treatment increases the sub-$G_0$-$G_1$ cell population, which is indicative of cellular apoptosis. FIG. 3D shows that selenocoxib-1-GSH arrested melanoma cells in the $G_0$-$G_1$ phase of the cell cycle. 1205 Lu and UACC 903 cells are treated with 12.5 and 25 µmol/L of celecoxib, selenocoxib-1-GSH or vehicle DMSO control for 72 h. Total floating and adherent cells are collected, and stained with propidium iodide to analyze the distribution of cells in different phases of the cell cycle stages using a FACScan analyzer. Selenocoxib-1-GSH, but not celecoxib treatment, inhibits cell cycle progression by increasing the sub-$G_0$-$G_1$ population and arresting cells in the $G_0$-$G_1$ phases of the cell cycle. Data represents an average of 2 independent experiments.

TABLE II

|  | FOM103 | FF2441 | WM35 | WM115 | UACC 903 | 1205 Lu | |
| --- | --- | --- | --- | --- | --- | --- | --- |
| Celecoxib | >100 | >100 | 51.3 ± 2.3 | 54.4 ± 3.6 | >100 | >100 | 24 h |
| Selenocoxib-1-GSH | 66.3 ± 3.0 | >100 | 52.6 ± 3.8 | 30.1 ± 3.3 | 30.9 ± 2.8 | 24.6 ± 2.2 | |
| Celecoxib | >100 | >100 | 42.3 ± 1.8 | 45.3 ± 2.7 | >100 | 83.6 ± 3.3 | 48 h |
| Selenocoxib-1-GSH | 53.4 ± 4.3 | 75.5 ± 5.6 | 4.1 ± 0.8 | 5.8 ± 0.9 | 20.6 ± 1.7 | 17.2 ± 1.6 | |
| Celecoxib | 68.0 ± 1.2 | 65.3 ± 3.3 | 37.9 ± 3.3 | 41.8 ± 2.9 | 76.6 ± 4.4 | 66.1 ± 3.2 | 72 h |
| Selenocoxib-1-GSH | 41.2 ± 3.2 | 36.3 ± 5.6 | 2.7 ± 0.4 | 3.1 ± 0.4 | 14.2 ± 1.2 | 10.6 ± 2.6 | |
|  | Normal | | Radial | Vertical | Metastatic | | |

Mechanisms leading to cell growth inhibition after treatment with selenocoxib-1-GSH are examined by measuring the level of cell proliferation, apoptosis, and the percentage of cells in the various phases of the cell cycle.

Cellular proliferation and apoptosis rates are measured by seeding $5 \times 10^3$ cells in 96-well plates, followed by treatment for 72 h with celecoxib and selenocoxib-1-GSH. Percentage of proliferating and apoptotic cells are quantified by a colorimetric using cell proliferation ELISA BrdU kit (Roche The number of sub-$G_0$-$G_1$ population cells increases by 6.2 and 4.7-fold, respectively when 1205 Lu and UACC 903 cells are treated with 25 µmol/L selenocoxib-1-GSH (FIG. 3D). In addition, increase in the $G_0$-$G_1$ cell population is also observed with 12.5 and/or 25 µmol/L selenocoxib-1-GSH treatment in these cell lines (FIG. 3D). Thus, selenocoxib-1-GSH inhibits cellular proliferation and triggered apoptosis mediated through a $G_0$-$G_1$ block, resulting in fewer cells in S and $G_2$-M phases.

Figure 4A:
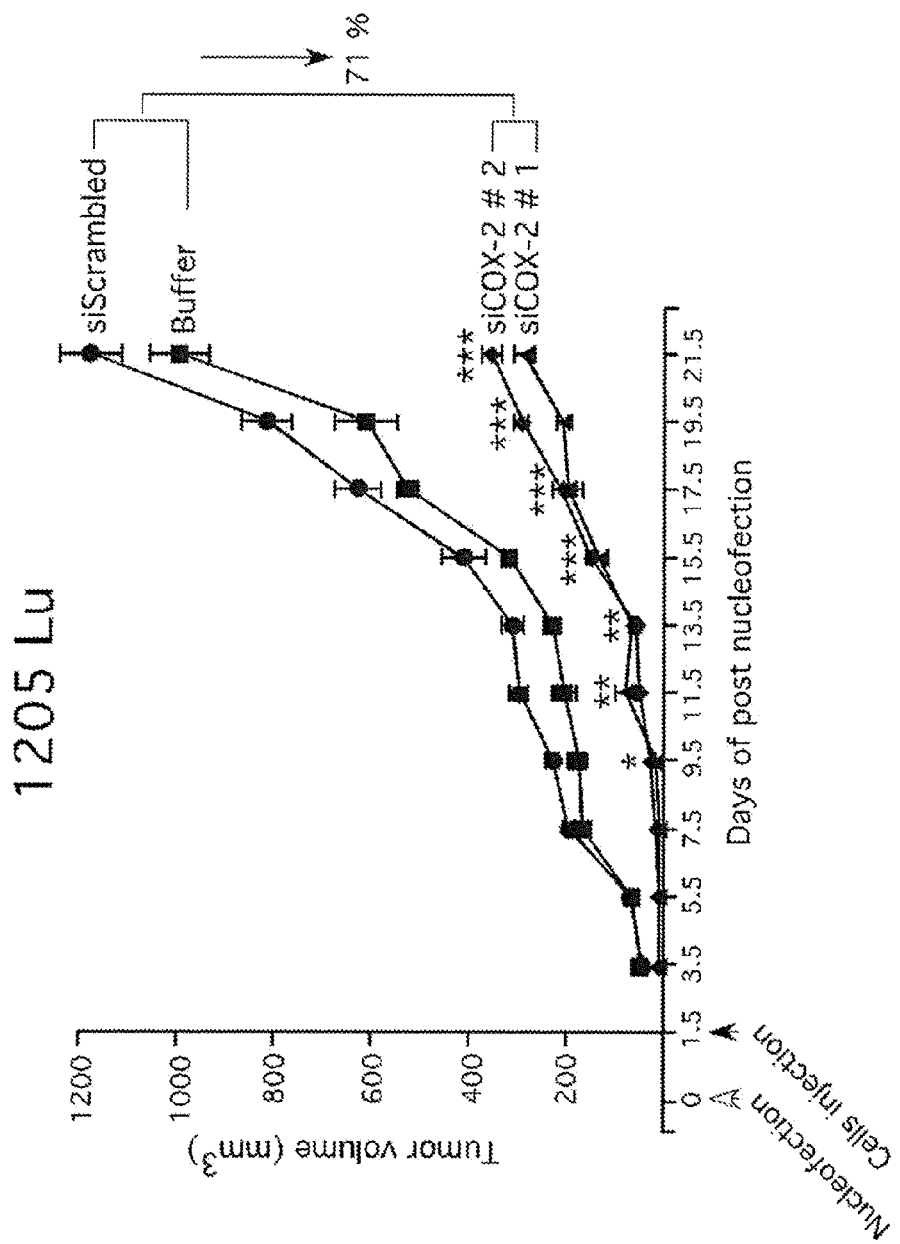
FIG. 4A is a graph showing that siRNA-mediated targeting of COX-2 decreases melanoma tumor development in mice.

Animal Studies Using siRNA Tumorigenicity Assessments:

Tumor kinetic studies are carried out in athymic-Foxn1$^{nu}$ nude mice (Harlan Sprague Dawley, IN). 200 pmoles of siRNA COX-2 #1 or COX-2 #2 are nucleofected into 2×10$^6$ 1205 Lu cells and after 48 h of recovery, 1×10$^6$ cells are collected in 0.2 mL of 10% FBS-DMEM and injected subcutaneously above both the left and right rib cages of 4-6 week old female mice (5 mice/group). Dimensions of developing tumors are measured on alternate days up to day 21.5, using calipers by L×W×D (mm$^3$) as described in Sharma A, et al., Clin Cancer Res 2009; 15:1674-85.

siRNA targeting COX-2 is used to reduce protein expression in melanoma cells to measure the effect on melanoma tumor development. 1205 Lu melanoma cells are nucleofected with siRNA targeting COX-2. 48 h later, viable cells are subcutaneously injected into left and right flanks of nude mice. Developing tumors are measured on alternate days for 21.5 days (FIG. 4A). The tumorigenic potential of COX-2 treated cells decreased by ~70% compared to buffer or scrambled siRNA control cells. Inhibition of COX-2 protein expression using siRNAs, reduces xenografted melanoma tumor development by an average of 71% after 21 days compared to control buffer and siScrambled treated tumors. FIG. 4A shows that siRNA-mediated targeting of COX-2 decreases melanoma tumor development in mice.

Selenocoxib-1-GSH inhibits melanoma tumor development in mice without significant toxicity.

Tumor kinetics are measured by subcutaneous injection of 1×10$^6$ 1205 Lu or UACC 903 cells in 0.2 mL of DMEM supplemented with 10% FBS subcutaneously injected above both left and right rib cages of 3- to 4-wk-old female athymic-Foxn1$^{nu}$ nude mice (Harlan Sprague Dawley, IN). Six days later, when a fully vascularized tumor (50-75 mm$^3$) had formed, mice are randomly divided into DMSO vehicle control and experimental groups (5 mice/group; 2 tumors/mouse) and treated intraperitoneally with selenocoxib-1-GSH (0.127 µmoles, equivalent to 10 ppm selenium) or celecoxib (0.127 µmoles) in DMSO on alternate days for 4 weeks. Body weight (grams) and dimensions of the developing tumors (mm$^3$) are measured at the time of drug treatment as described in Sharma A, et al., Clin Cancer Res 2009; 15:1674-85; and Madhunapantula S V, et al., Mol Cancer Ther 2008; 7:1297-308.

Figure 4B:
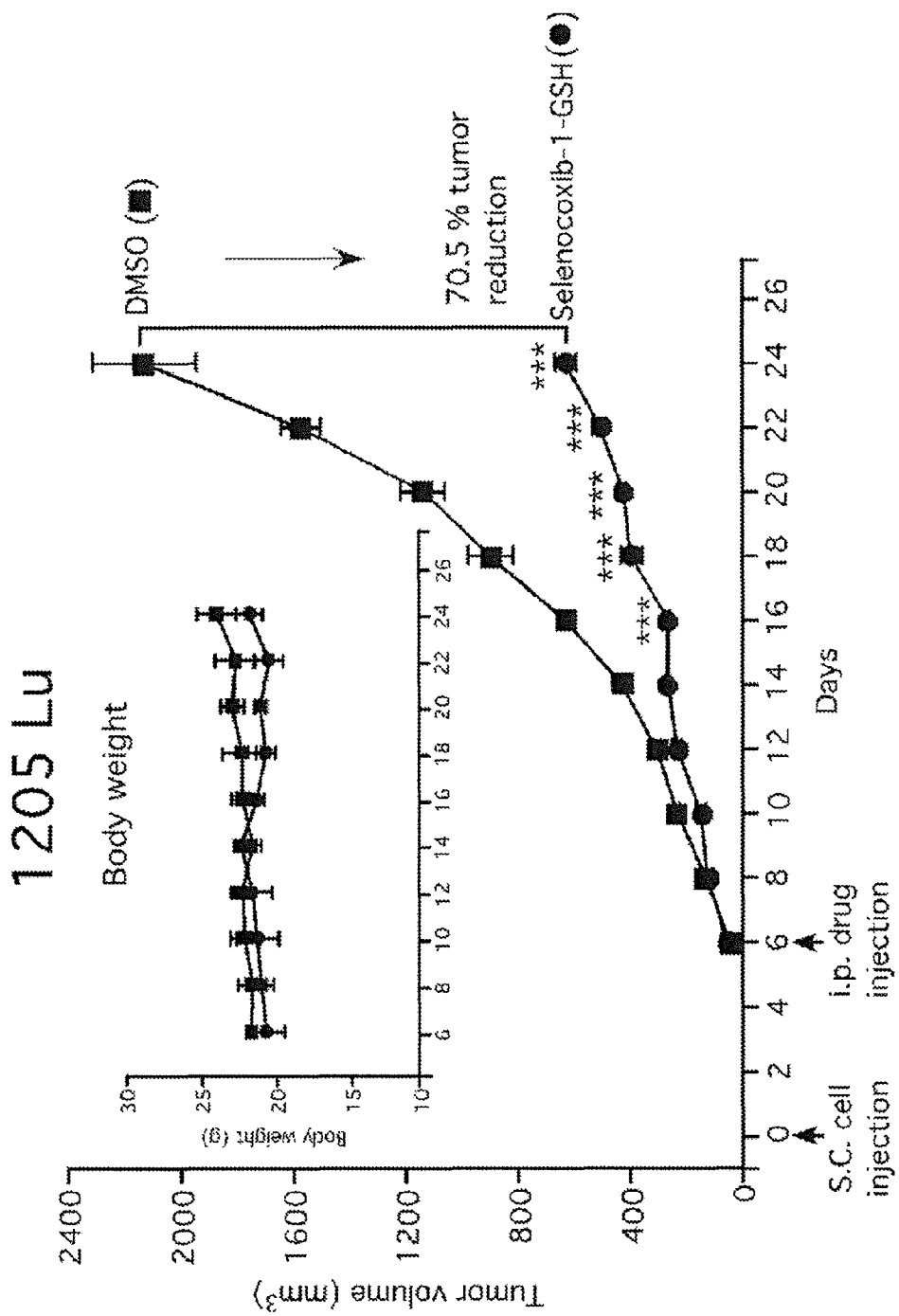
FIG. 4B is a graph showing a significant decrease in xenograft tumor development compared to vehicle DMSO treated mice is observed from day 16 in 1205 Lu tumors, and a decrease in tumor volume is observed, following selenocoxib-1-GSH treatment compared to controls, with no noticeable changes in animal body weight.
Figure 4C:
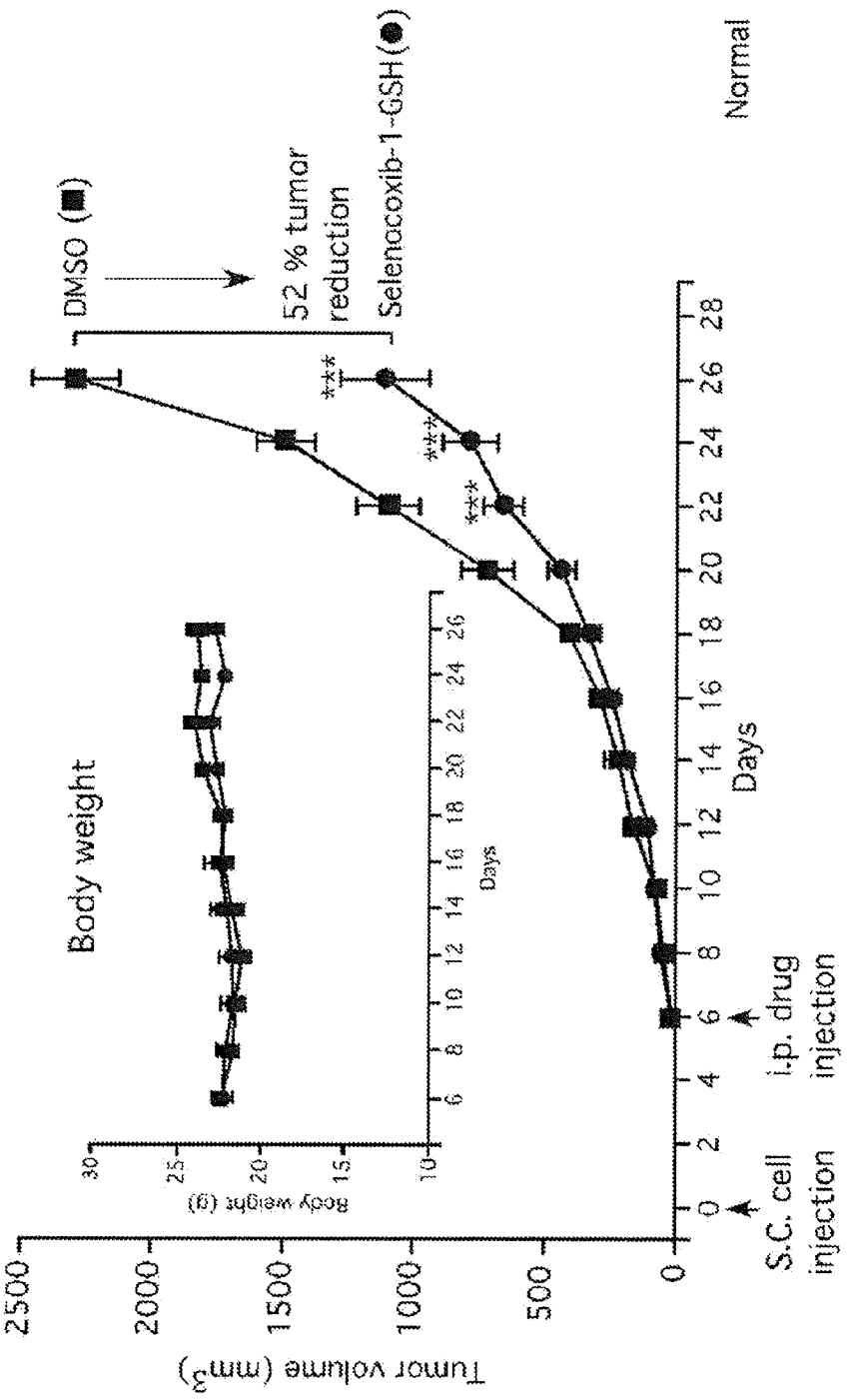
FIG. 4C is a graph showing a significant decrease in xenograft tumor development compared to vehicle DMSO treated mice is observed in UACC 903 tumors from day 22, and a decrease in tumor volume is observed, following selenocoxib-1-GSH treatment compared to controls, with no noticeable changes in animal body weight.

FIGS. 4B and 4C show results of this in vivo analysis. Selenocoxib-1-GSH reduces tumor development by 70.5% and 52% in 1205 Lu and UACC 903 cells respectively, compared to DMSO control treated mice (P<0.001; two-way ANOVA). No significant difference is observed in body weight of mice treated with the drug indicating negligible toxicity (FIGS. 4B and 4C; inset).

A significant decrease in xenograft tumor development compared to vehicle DMSO treated mice is observed from day 16 in 1205 Lu tumors, FIG. 4B. Similarly, a significant decrease is also observed in UACC 903 tumors from day 22, FIG. 4C. For both cell lines at the end of treatment, up to a 70% decrease in tumor volume is observed following selenocoxib-1-GSH treatment compared to controls, FIGS. 4B and 4C. No noticeable changes in animal body weight are observed, FIGS. 4B and 4C; inset.

Toxicity Assessments

Four to six week old athymic-Foxn1$^{nu}$ nude mice (Harlan Sprague Dawley, IN), are treated with either vehicle control or selenocoxib-1-GSH (n=5) as described in tumor kinetics studies. At the end of treatment, blood is collected from each sacrificed animal in a plasma separator tube with lithium heparin (BD Microtainer) following cardiac puncture and analyzed for ALKP (Alkaline phosphatase), ALT (Alanine aminotransferase), AST (Aspartate aminotransferase), ALB (Total albumin), TBIL (Total bilirubin), CREA (Creatinine), BUN (Blood urea nitrogen), CHOL (Total cholesterol), TRIG (Total triglyceride) and GLU (Glucose) levels to ascertain possible liver, heart, kidney, and pancreas related toxicity. A portion of vital organs, liver, heart, kidney, pancreas, and spleen-from each animal is formalin-fixed and paraffin-embedded to examine toxicity-associated changes in cell morphology and tissue organization following H&E staining as described in Nguyen N, et al. Cancer Prev Res (Phila) 2011; 4: 248-58.

Figure 4D:
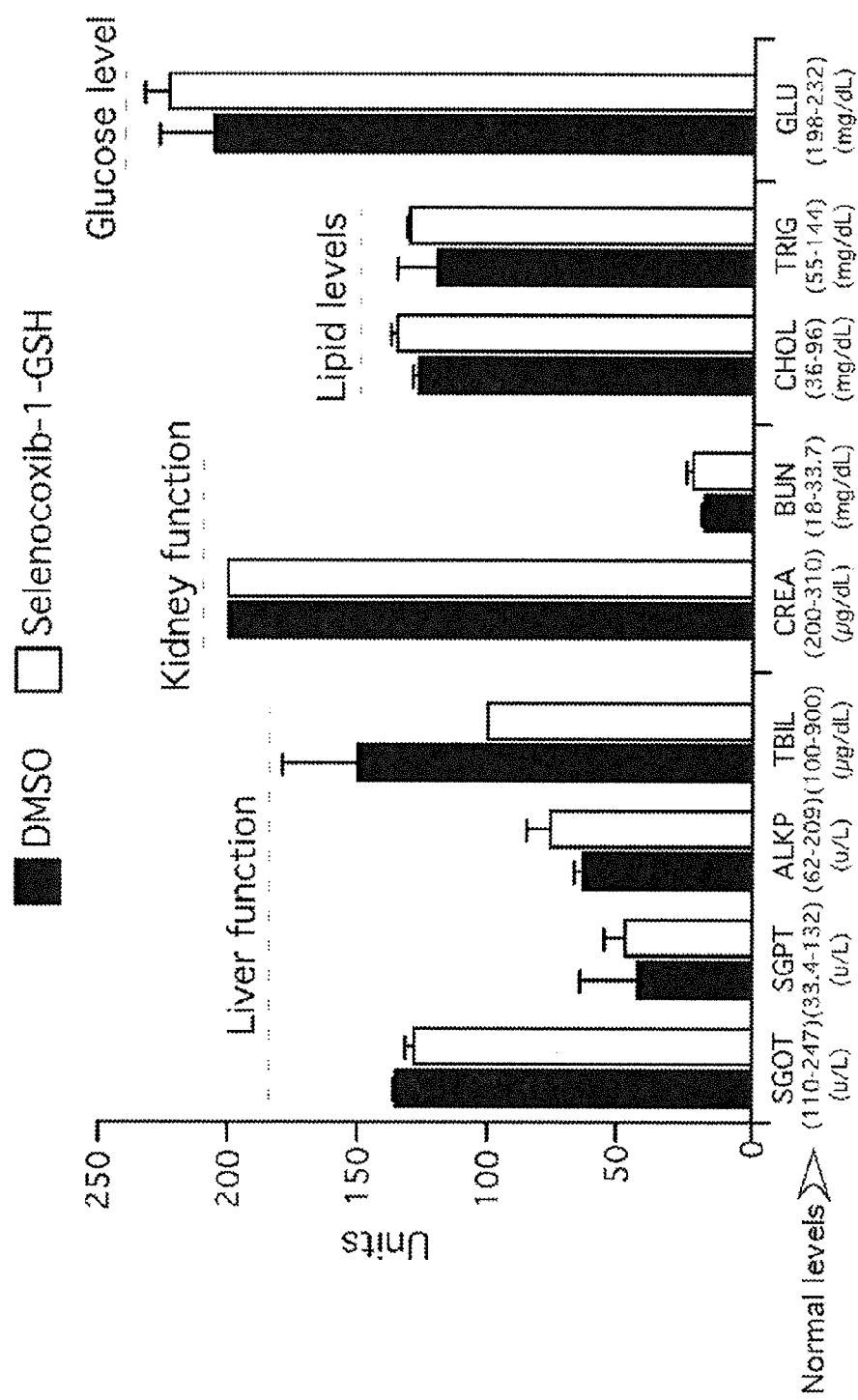
FIG. 4D is a graph showing that selenocoxib-1-GSH does not affect blood biomarkers indicative of major organ related toxicity.

The levels of blood markers for major organ related toxicity, ALKP (Alkaline phosphatase), ALT (Alanine aminotransferase), AST (Aspartate aminotransferase), ALB (Total albumin), TBIL (Total bilirubin), CREA (Creatinine), BUN (Blood urea nitrogen), CHOL (Total cholesterol), TRIG (Total triglyceride) and GLU (Glucose) are evaluated and levels indicate negligible differences compared to controls at the concentrations examined. FIG. 4D shows that selenocoxib-1-GSH does not affect blood biomarkers indicative of major organ related toxicity. The levels of blood markers for major organ related toxicity, ALKP (Alkaline phosphatase), ALT (Alanine aminotransferase), AST (Aspartate aminotransferase), ALB (Total albumin), TBIL (Total bilirubin), CREA (Creatinine), BUN (Blood urea nitrogen), CHOL (Total cholesterol), TRIG (Total triglyceride) and GLU (Glucose) are evaluated and levels indicate negligible differences compared to controls at the concentrations examined.

Figure 5:
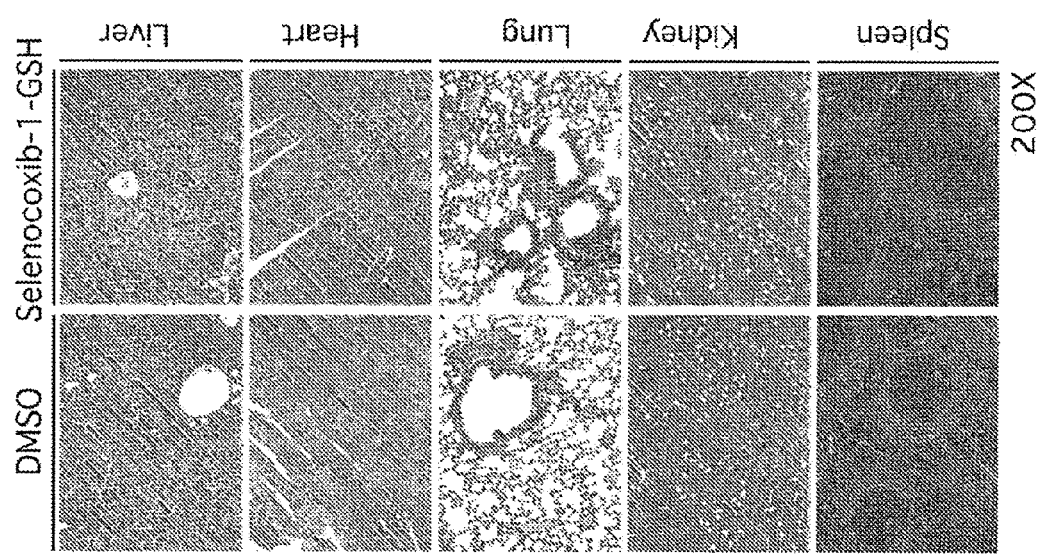
FIG. 5 shows images of H&E stained tissue sections from control DMSO vehicle or selenocoxib-1-GSH treated mice showing no changes in the morphology or architecture of the liver, heart, lung, kidney or spleen and demonstrating that selenocoxib-1-GSH effectively inhibits melanoma tumor development leading to tumor regression without significant organ related toxicity.

Analysis of H&E stained tissue sections from control DMSO vehicle or selenocoxib-1-GSH treated mice show no changes in the morphology or architecture of the liver, heart, lung, kidney or spleen. These data, in FIG. 5, demonstrate that selenocoxib-1-GSH effectively inhibits melanoma tumor development leading to tumor regression without significant organ related toxicity.

Signaling Pathways

Figure 6A:
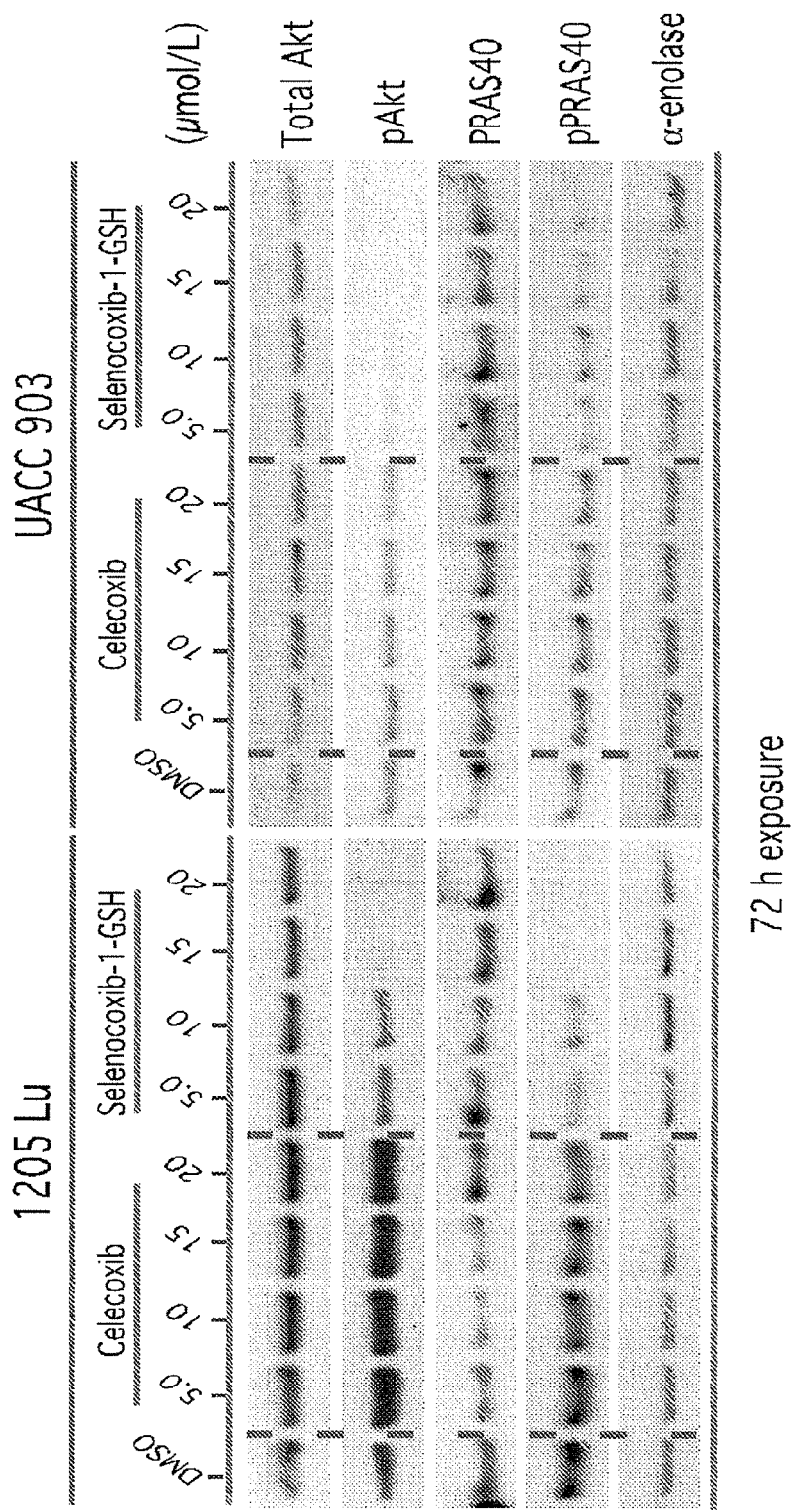
FIG. 6A is a graph showing that selenocoxib-1-GSH inhibits the PI3K/Akt signaling pathway.

Selenocoxib-1-GSH inhibits Akt signaling, which activates MAP kinase activity to reduce melanoma cellular proliferation and promote apoptosis.

pAkt levels are examined in 1205 Lu and UACC 903 melanoma cells following treatment. Compared to celecoxib, selenocoxib-1-GSH treatment inhibited the Akt phosphorylation in a dose dependent manner (FIG. 6A). FIG. 6A shows that selenocoxib-1-GSH inhibits the PI3K/Akt signaling pathway. 1205 Lu and UACC 903 cells are treated with increasing concentrations of celecoxib and selenocoxib-1-GSH for 72 h and cell lysates analyzed to determine expression as well as activity of Akt signaling proteins. Selenocoxib-1-GSH reduces expression of phosphorylated Akt, pPRAS40. Alpha-enolase serves as a control for equal protein loading.

Figure 6B:
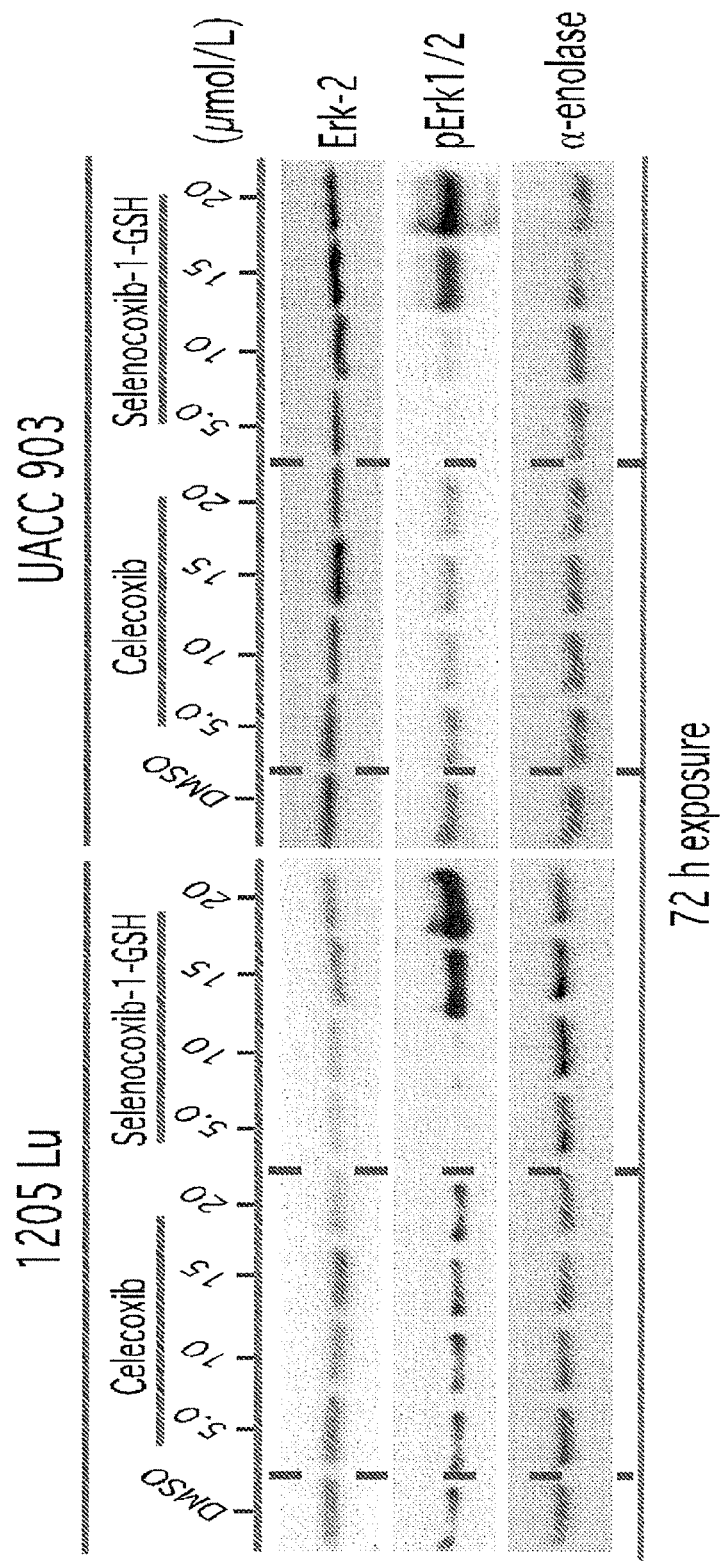
FIG. 6B is a graph showing that selenocoxib-1-GSH activates the MAPK signaling pathway
Figure 6C:
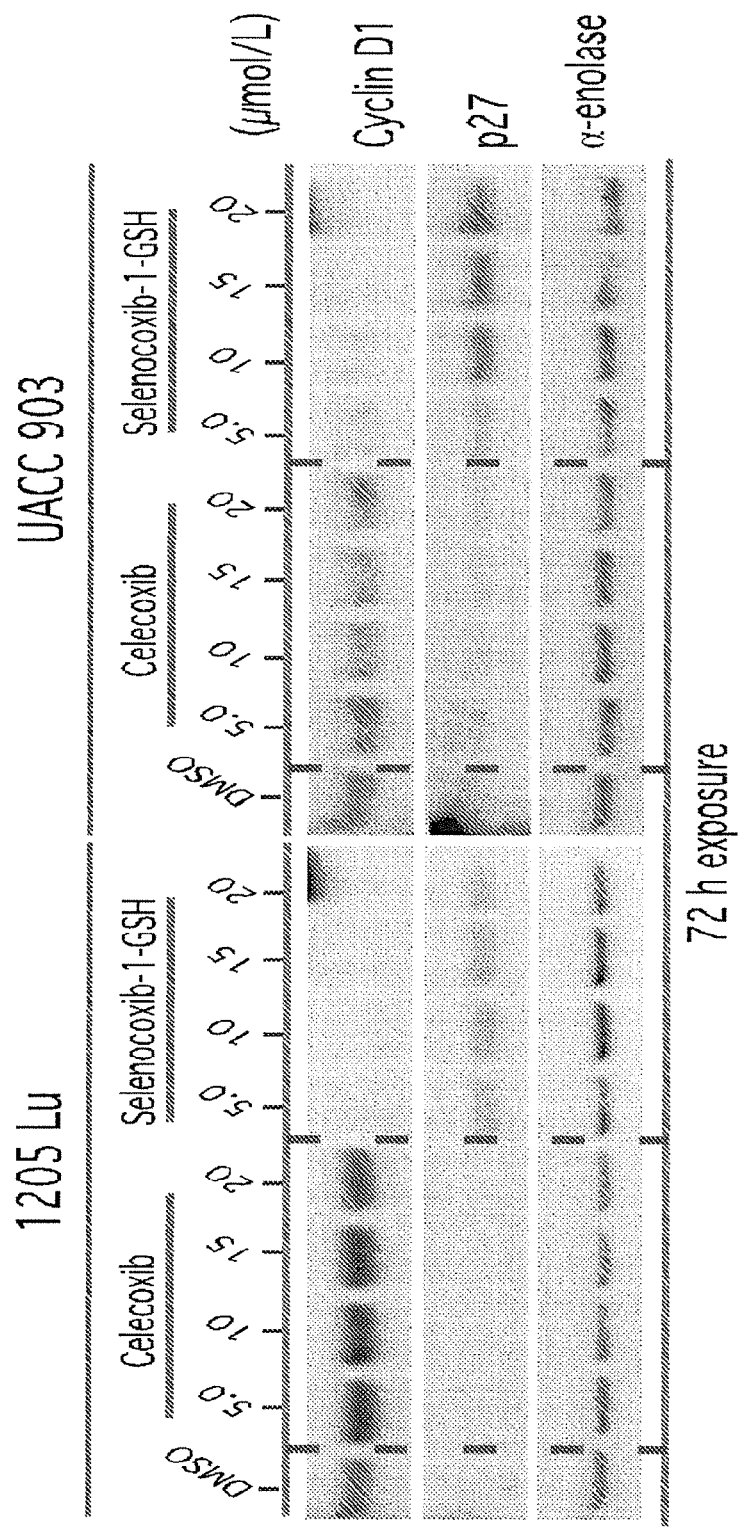
FIG. 6C is a graph showing that selenocoxib-1-GSH inhibits protein indicating cell proliferation.

Furthermore, phosphorylation of the downstream Akt3 substrate PRAS40 was significantly inhibited, FIG. 6A 1205 Lu and UACC 903 melanoma cells have elevated MAPK activities due to presence of constitutively active $^{V600E}$B-Raf. Akt3 phosphorylates $^{V600E}$B-Raf to lower MAP kinase pathways activity to levels promoting rather than inhibiting cellular proliferation. FIG. 6B shows that selenocoxib-1-GSH activates the MAPK signaling pathway. Selenocoxib-1-GSH treatment at 15 and 20 µmol/L in both 1205 Lu and UACC 903 cell lines increased pErk1/2 levels. Alpha-enolase serves as a control for equal protein loading. Therefore, selenocoxib-1-GSH treatment at 15 and 20 µmol/L concentrations in both 1205 Lu and UACC 903 cell lines leads to higher pERK1/2 levels, FIG. 6B, due to decreased phosphorylation and regulation of $^{V600E}$B-Raf by Akt (Cheung et al., Cancer Res. 68:3429-3439, 2008). In addition, selenocoxib-1-GSH also inhibits the expression of cyclin-D1 and increases the levels of p27, FIG. 6C. FIG. 6C shows that selenocoxib-1-GSH inhibits protein indicating cell proliferation. Cyclin D1 levels decreased with a concomitant increase in p27 following treatment with selenocoib-1-GSH. Alpha-enolase serves as a control for equal protein loading.

Figure 6D:
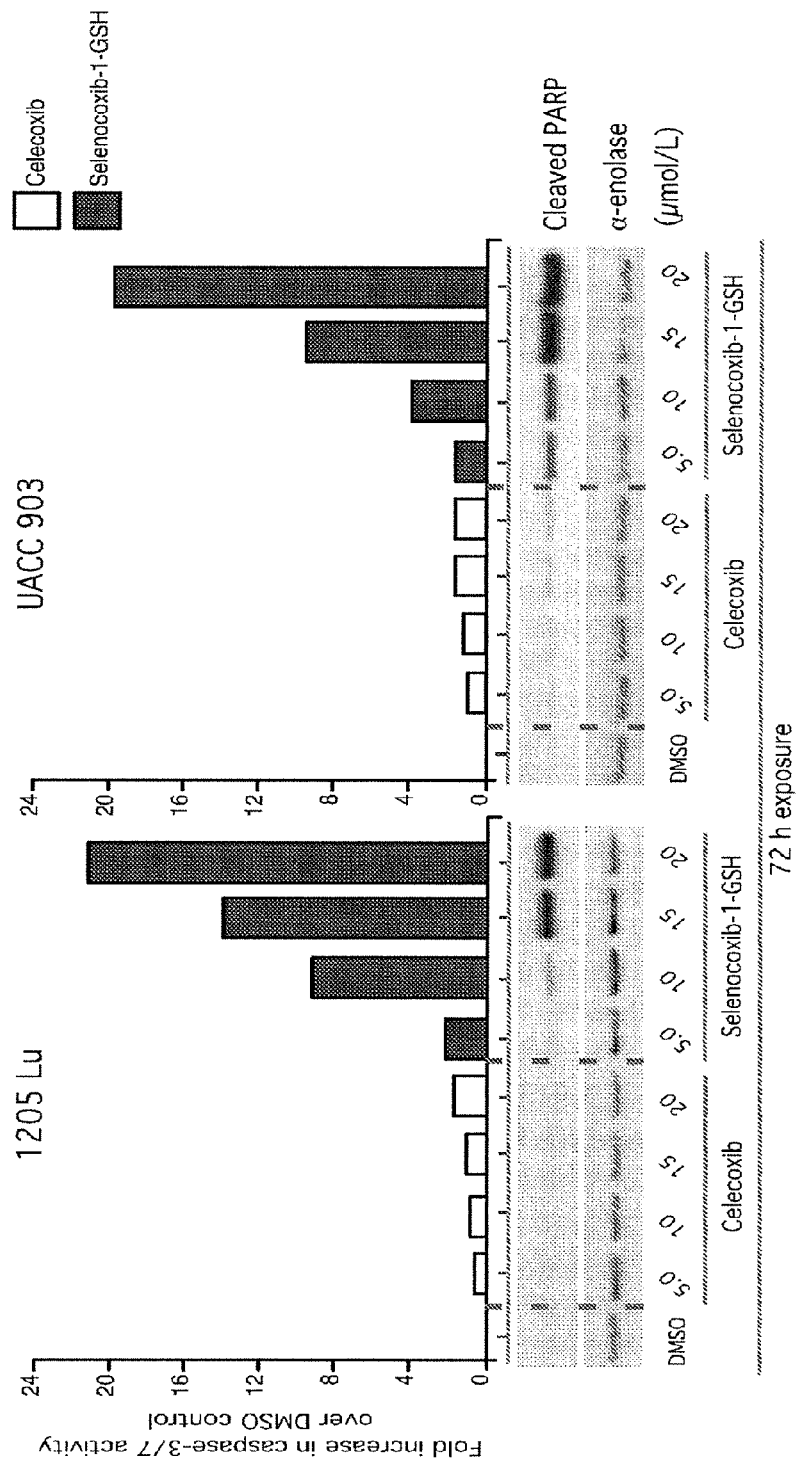
FIG. 6D is a graph showing that selenocoxib-1-GSH increased protein cleavage indicating apoptosis.

Finally, increased caspase 3/7 and cleaved PARP levels are observed indicating higher levels of apoptosis in selenocoxib-1-GSH compared to celecoxib treated cells, FIG. 6D. FIG. 6D shows that selenocoxib-1-GSH increased protein cleavage indicating apoptosis. Selenocoxib-1-GSH increases caspase-3/7 activity and elevates levels of cleaved PARP protein in melanoma cells. Alpha-enolase serves as a control for equal protein loading.

Reactive Oxygen Species (ROS) Assay

Figure 7A:
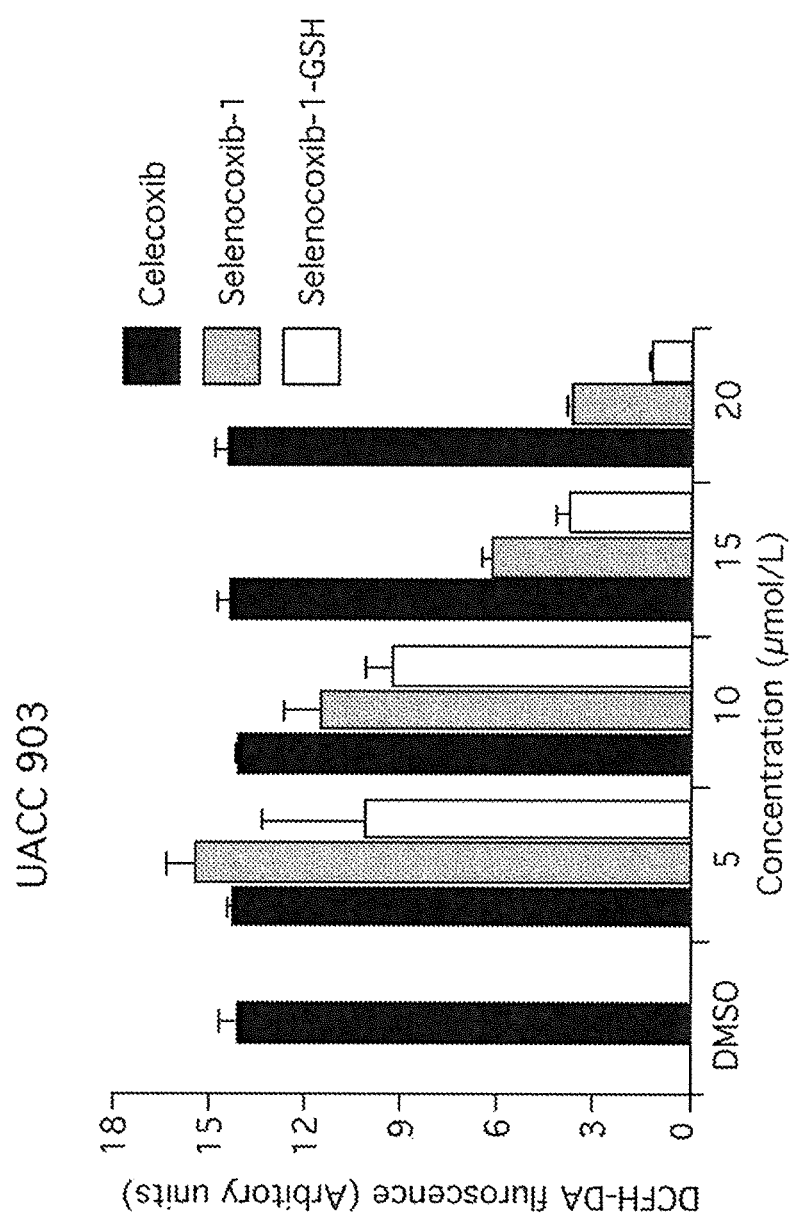
FIG. 7A is a graph showing that selenocoxib-1-GSH more dramatically decreased ROS compared to celecoxib and selenocoxib-1 in UACC 903 melanoma cells.
Figure 7B:
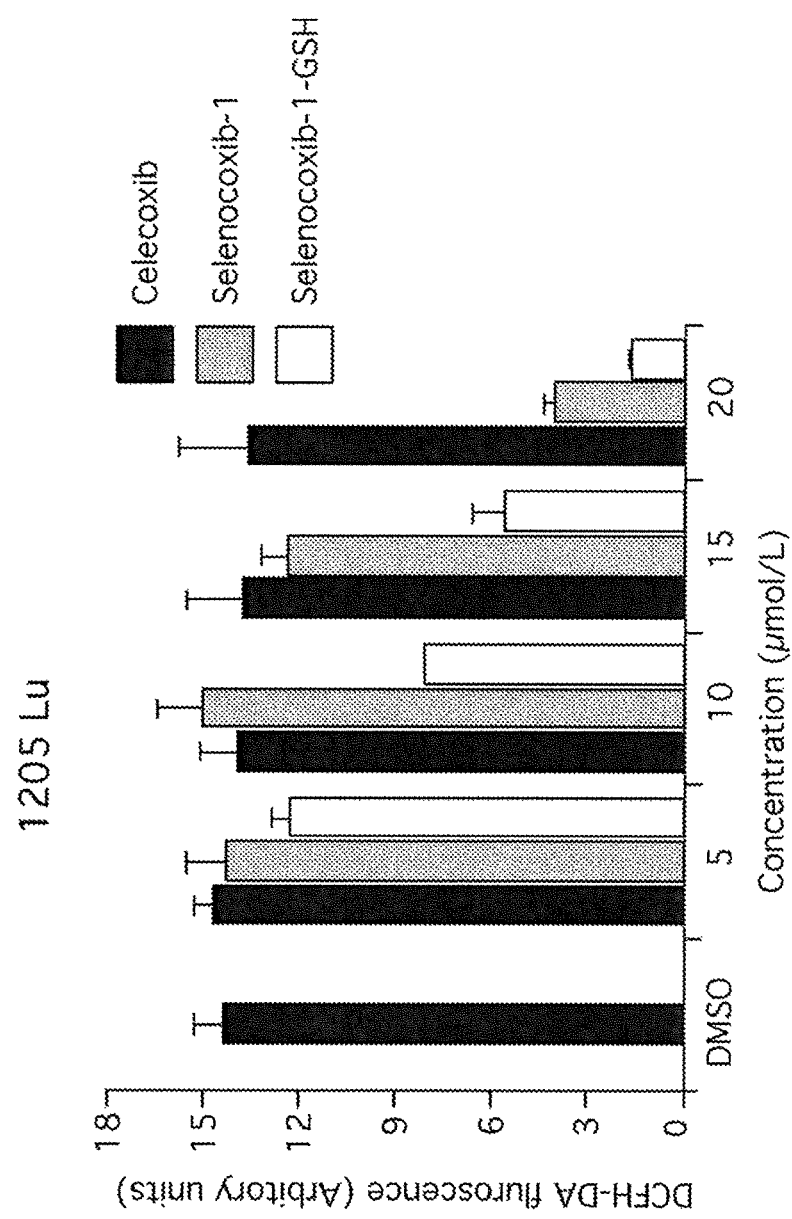
FIG. 7B is a graph showing that selenocoxib-1-GSH more dramatically decreased ROS compared to celecoxib and selenocoxib-1 in 1205 Lu melanoma cells.

Intracellular ROS are monitored according to a procedure described in detail in Smasundaram et al., Cancer Res., 62:3868-3875, 2002. $1.5 \times 10^6$ melanoma cells are plated in 100 mm culture dishes and 48 hours later treated with 5-20 micromoles/liter concentration of celecoxib, selenocoxib-1 or selenocoxib-1-GSH. After 24 hours treatment, total cells (floating and adherent) are collected in ice-cold phosphate-buffered saline and $5 \times 10^3$ cells/well placed in 100 microliters culture medium in a 96-well plate containing 10 micromoles/liter 2',7'-dichlorfluorescein-diacetate (commercially available from Sigma, St. Louis, Mo.) and incubated at 37° C. for 30 minutes. The amount of ROS present compared to DMSO vehicle treated cells was represented in arbitrary units. The assay is performed twice with four replicates each time, results are shown in FIGS. 7A and 7B.

Selenocoxib-1-GSH inhibits the generation of ROS. UACC 903 and 1205 Lu cells were exposed to celecoxib, selenocoxib-1 and selenocoxib-1-GSH at 5, 10, 15 and 20 µmol/L. Generation of ROS was assayed using dichiorodihydrofluorescein diacetate (DCFH-DA) and fluorescence measured at an emission wavelength of 530 nm and excitation wavelength of 485 nm. The GSH form of selenocoxib-1 more dramatically decreased ROS than the forms lacking it (FIGS. 7A and 7B).

Synthesis of a Liposomal Formulation of Selenocoxib-1-GSH

Selenocoxib-1-GSH can be encapsulated into nanoliposomes by combining L-α-phosphatidylcholine (ePC) and 1,2-dipalmitoyl-sn-Glycero-3-Phosphoethanolamine-N-[methoxy(polyethylene glycol)-2000] ammonium salt (DPPE-PEG-2000) in chloroform at 80:20 mol % and a final lipid concentrations 25 mg/mL in buffer solution (Avanti Polar Lipids Inc-Alabaster, Ala.). 5.0 mg of selenocoxib-1-GSH will be added to 1 milliliter of nanoliposome solution, the mixture dried under nitrogen gas and resuspended in 0.9% saline at room temperature to 60° C. Following rehydration, the material will be sonicated at 60° C. for 30 minutes followed by extrusion at 60° C. through a 100-nm polycarbonate membrane using Avanti Mini Extruder (Avanti Polar Lipids Inc-Alabaster, Ala.). Analysis of particle size and charge of nanoliposomes will be performed by using a Malvern Zetasizer Nano, Malvern Instruments, UK). Liposomes containing selenocoxib-1-GSH according to this protocol will be homogenously distributed in nanosize range of 70-80 nm with a neutral surface charge. Determination of encapsulation efficiency of selenocoxib-1-GSH into nanoliposomes will be based on UV-visible spectrophotometry and drug loading calculated through % of encapsulation efficiency (total drugs–free drugs/total drugs×10). Size exclusion chromatography and dialysis will be used to removing free compound. Drug loading of greater or equal to 60% is predicted.

Therapeutic universality of selenocoxib-1-GSH for killing cancer cells is examined by treating pancreatic (MiaPaca-2), breast (MDA-MB-231), prostate (PC-3) or sarcoma (HT-1080) and colon (Caco2) cell. lines with the drug and establishing the IC50 for each cell line, Table III. Selenocoxib-1-GSH kills the various cancer cell lines at 2-3-fold lower concentrations than normal fibroblast cells.

TABLE III

| Cell lines | Celecoxib | Selenocoxib-1-GSH |
| --- | --- | --- |
| MDA-MB-231 (Breast) | >100 | 15.4 ± 2.51 |
| PC-3 (Prostate) | >100 | 16.4 ± 2.11 |
| MiaPaca-2 (Pancreas) | >100 | 13.3 ± 1.01 |
| HT-1080 (Fibro sarcoma) | >100 | 9.1 ± 1.89 |
| Caco-2 (Colon) | >100 | 16.1 ± 0.87 |

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A composition comprising:
   a selenium-containing COX-2 inhibitor, wherein the selenium-containing COX-2 inhibitor is selenocoxib-1-cysteine.

2. A pharmaceutical composition, comprising:
   a selenium-containing COX-2 inhibitor selected from the group consisting of: selenocoxib-1-cysteine, selenocoxib-1-NAC, and a mixture thereof; and
   a pharmaceutically acceptable carrier, wherein the pharmaceutically acceptable carrier comprises a particulate carrier.

3. The pharmaceutical composition of claim 2, wherein the pharmaceutical composition is formulated for topical application.

4. The pharmaceutical composition of claim 2, further comprising an additional therapeutic agent.

5. A pharmaceutical composition, comprising:
   a selenium-containing COX-2 inhibitor selected from the group consisting of: selenocoxib-1-cysteine, selenocoxib-1-NAC, and a mixture thereof; and
   a pharmaceutically acceptable carrier, wherein the pharmaceutically acceptable carrier comprises a nanoparticulate carrier.

6. The pharmaceutical composition of claim 5, wherein the pharmaceutical composition is formulated for topical application.

7. The pharmaceutical composition of claim 5, further comprising an additional therapeutic agent.

8. A pharmaceutical composition comprising a selenium-containing COX-2 inhibitor selected from the group consisting of: selenocoxib-1-cysteine, selenocoxib-1-NAC, and a mixture thereof; and
   a pharmaceutically acceptable carrier,
   wherein the pharmaceutical composition comprises a plurality of nanoliposomes, the nanoliposomes comprising selenocoxib-1-cysteine, selenocoxib-1-NAC or a mixture thereof, the nanoliposomes having an average particle size in the range of 1-100 nm.

9. The pharmaceutical composition of claim 8, wherein the pharmaceutical composition is formulated for topical application.

10. The pharmaceutical composition of claim 8, further comprising an additional therapeutic agent.

* * * * *